United States Patent
Leslie et al.

(10) Patent No.: US 9,681,963 B2
(45) Date of Patent: Jun. 20, 2017

(54) BONE SIZING GUIDE

(71) Applicant: DEPUY IRELAND UNLIMITED COMPANY, Ringaskiddy (IE)

(72) Inventors: Ian Leslie, Leeds (GB); Michael Reeve, Tadcaster (GB); Michael Rock, Leeds (GB)

(73) Assignee: DEPUY IRELAND UNLIMITED COMPANY, Cork (IE)

( * ) Notice: Subject to any disclaimer, the term of this patent is extended or adjusted under 35 U.S.C. 154(b) by 522 days.

(21) Appl. No.: 14/357,258

(22) PCT Filed: Oct. 18, 2012

(86) PCT No.: PCT/GB2012/052571
§ 371 (c)(1),
(2) Date: May 9, 2014

(87) PCT Pub. No.: WO2013/068720
PCT Pub. Date: May 16, 2013

(65) Prior Publication Data
US 2015/0173774 A1    Jun. 25, 2015

(30) Foreign Application Priority Data

Nov. 11, 2011 (GB) .................................... 1119481.8
Mar. 28, 2012 (GB) .................................... 1205411.0

(51) Int. Cl.
*A61B 17/15* (2006.01)
*A61F 2/46* (2006.01)
(Continued)

(52) U.S. Cl.
CPC .......... *A61F 2/4657* (2013.01); *A61B 17/155* (2013.01); *A61B 90/06* (2016.02);
(Continued)

(58) Field of Classification Search
CPC ............... A61B 17/1764; A61F 2/4657; A61F 2002/4658
(Continued)

(56) References Cited

U.S. PATENT DOCUMENTS 4,703,751 A   11/1987  Pohl
5,364,401 A   11/1994  Ferrante
(Continued)

FOREIGN PATENT DOCUMENTS

EP      791334 A1    8/1997
FR     2813780 A1    3/2002
(Continued)

OTHER PUBLICATIONS

Japanese Search Report for Application No. 2014-540548, Mail Date Aug. 23, 2016, 2 pages.
(Continued)

*Primary Examiner* — Christian Sevilla
*Assistant Examiner* — Eric S Gibson

(57) ABSTRACT

A bone sizing guide for assessing the size of an end of a bone includes a body (6) having a foot component (2) with a first surface (10) to rest against an end surface of the bone and a foot (12) extending transverse to the first surface to contact a side surface of the bone. A superstructure (40) is coupled to the body so that the superstructure can slide relative to the body towards and away from the body, at least one of the superstructure and the body being adjustable so that the rotational direction in which the superstructure extends relative to the foot component about a first axis extending transverse to the first surface is adjustable. A stylus (53) extends from the superstructure transverse to the first surface of the body, the stylus having a tip to contact a surface of the bone, and a scale (64) is coupled to or formed on a first one of the superstructure and the body. An indicator (52) is (Continued)

coupled to or formed on a second one of the superstructure and the body to identify a position on the scale. The identified position on the scale shifts as the superstructure slides towards or away from the body, and the identified position shifts as the superstructure rotates relative to the body without sliding motion between the superstructure and the body, such that the identified position on the scale is indicative of the distance between the stylus and the foot.

16 Claims, 10 Drawing Sheets

(51) Int. Cl.
*A61B 90/00* (2016.01)
*A61F 2/38* (2006.01)
*A61B 17/17* (2006.01)
*A61F 2/30* (2006.01)

(52) U.S. Cl.
CPC ..... *A61B 17/1764* (2013.01); *A61B 2090/061* (2016.02); *A61F 2/3859* (2013.01); *A61F 2002/30617* (2013.01); *A61F 2002/4658* (2013.01); *A61F 2250/0097* (2013.01)

(58) Field of Classification Search
USPC .......................................... 606/86 R–89, 102
See application file for complete search history.

(56) References Cited

U.S. PATENT DOCUMENTS

| | | | |
|---|---|---|---|
| 5,486,178 | A | 1/1996 | Hodge |
| 5,540,696 | A | 7/1996 | Booth, Jr. |
| 5,569,261 | A | 10/1996 | Marik |
| 5,688,279 | A | 11/1997 | McNulty |
| 5,688,280 | A | 11/1997 | Booth, Jr. |
| 5,776,137 | A * | 7/1998 | Katz .................. A61B 17/155 606/102 |
| 5,925,049 | A * | 7/1999 | Gustilo ............... A61B 17/155 606/82 |
| 6,013,081 | A * | 1/2000 | Burkinshaw ........ A61B 17/155 606/102 |
| 6,056,756 | A * | 5/2000 | Eng ..................... A61B 17/155 606/87 |
| 6,458,135 | B1 * | 10/2002 | Harwin ................ A61B 17/155 606/88 |
| 6,602,258 | B1 * | 8/2003 | Katz .................. A61B 17/154 606/80 |
| 7,261,719 | B1 * | 8/2007 | Twomey .............. A61B 5/1072 606/102 |
| 7,451,550 | B2 * | 11/2008 | Dees, Jr. ............ A61B 17/1764 33/512 |
| 7,488,324 | B1 * | 2/2009 | Metzger ............... A61B 17/155 33/511 |
| 8,382,764 | B2 | 2/2013 | Dower |
| 8,579,906 | B2 * | 11/2013 | Rangaiah ............. A61B 17/154 606/88 |
| 8,828,020 | B2 * | 9/2014 | Dower ................. A61B 5/1072 606/102 |
| 9,050,197 | B2 * | 6/2015 | Lorio ................... A61F 2/4657 |
| 9,113,913 | B2 * | 8/2015 | Reeve ................. A61B 17/155 |
| 9,216,026 | B2 * | 12/2015 | Reeve ................. A61B 17/155 |
| 9,314,351 | B2 * | 4/2016 | Dower ................. A61B 5/1072 |
| 2003/0149378 | A1 * | 8/2003 | Peabody ............. A61B 5/1072 600/587 |
| 2004/0215205 | A1 * | 10/2004 | Plumet ................ A61B 17/155 606/102 |
| 2004/0220583 | A1 * | 11/2004 | Pieczynski, II .... A61B 17/1764 606/102 |
| 2005/0049603 | A1 * | 3/2005 | Calton ................ A61B 17/157 606/87 |
| 2005/0209600 | A1 * | 9/2005 | Fencl .................. A61B 17/155 606/89 |
| 2006/0142778 | A1 * | 6/2006 | Dees, Jr. ............ A61B 17/1764 606/88 |
| 2006/0184173 | A1 | 8/2006 | Collazo |
| 2006/0241634 | A1 | 10/2006 | Tuttle |
| 2007/0173851 | A1 * | 7/2007 | McMillen .......... A61B 17/1764 606/87 |
| 2007/0233140 | A1 | 10/2007 | Metzger |
| 2008/0161824 | A1 * | 7/2008 | McMillen ............ A61B 17/155 606/102 |
| 2010/0286524 | A1 | 11/2010 | Daoura |
| 2010/0324563 | A1 * | 12/2010 | Green, II ............. A61F 2/4657 606/89 |
| 2011/0046685 | A1 * | 2/2011 | Faure .................. A61B 17/155 606/86 R |
| 2012/0143205 | A1 * | 6/2012 | Dower ................. A61B 5/1072 606/102 |
| 2013/0066322 | A1 * | 3/2013 | Chana .................. A61F 2/4657 606/91 |
| 2013/0144302 | A1 * | 6/2013 | Reeve ................. A61B 17/155 606/102 |
| 2014/0025081 | A1 * | 1/2014 | Lorio ................... A61F 2/4657 606/102 |
| 2014/0148811 | A1 * | 5/2014 | Reeve ................. A61B 17/155 606/88 |
| 2014/0343562 | A1 * | 11/2014 | Dower ................. A61B 5/1072 606/102 |
| 2015/0173774 | A1 * | 6/2015 | Leslie ................. A61B 17/155 606/102 |
| 2015/0209158 | A1 * | 7/2015 | Reeve ................. A61F 2/4657 623/20.35 |
| 2015/0335448 | A1 * | 11/2015 | Lorio ................... A61F 2/4657 606/88 |
| 2016/0135825 | A1 * | 5/2016 | Toler ................... A61B 17/025 606/88 |
| 2016/0199134 | A1 * | 7/2016 | Brown ................. A61B 19/50 703/1 |
| 2016/0296243 | A1 * | 10/2016 | Green, II .......... A61B 17/1764 |
| 2016/0361178 | A1 * | 12/2016 | Budhabhatti ...... A61B 17/1764 |

FOREIGN PATENT DOCUMENTS

| | | |
|---|---|---|
| JP | 8-308857 A | 11/1996 |
| JP | 09006066 A | 1/2009 |
| JP | 11-78529 A | 4/2011 |
| WO | WO 2006069336 A1 | 6/2006 |
| WO | WO 2011141722 A1 | 11/2011 |
| WO | WO 2011141723 A1 | 11/2011 |

OTHER PUBLICATIONS

UK Search Report GB1119481.8 dated Feb. 22, 2012.
PCT Search Report PCT/GB2012/052571 dated Jan. 4, 2013.
The Concept of Personalization, Legend II Surgical Technique, The AMK Total Knee System Instrumentation, 20M0392, 0601-12, 1992 (31 pages).
Legend II Surgical Technique, AMK Total Knee System Using AMK Legend II Instruments, 1M800, 0601-12-000 (Rev. 6) 1998 29 pages.
PFC Sigma RP-F Specialist Instruments Surgical Technique, 9090-12-000 Version 2, 2004, 32 pages.
Surgical Technique for Use With P.F.C. Knee Systems, Johnson & Johnson Orthopaedics, Primary Cruciate-Retaining Procedure, Specialist 2 Instruments, SP2-001, 1996, 61 pages.
Surgical Technique for Use With P.F.C. Sigma Knee Systems, Primary Cruciate-Retaining and Cruciate Substituting Procedure, Specialist 2 Instruments, SP2-007 Rev. 4, 1998, 106 pages.
Chinese Search Report for Application No. 201180023366.5, 13 pages.
Japanese Search Report for Application No. 2013-509613, Date Drafted Oct. 31, 2014, 11 pages.
Australian Search Report for Application No. 2011251778, Date of Issue Nov. 27, 2014, 4 pages.

(56) References Cited

OTHER PUBLICATIONS

Australian Search Report for Application No. 2011251779, Date of Issue May 27, 2014, 3 pages.
Japanese Search Report for Application No. 2013-509614, Date Drafted Dec. 5, 2014, 8 pages.
PCT International Search Report and Written Opinion PCT/GB2011/050582 Dated Jul. 27, 2011.
UK Search Report GB1007782.4 Dated Aug. 19, 2010.

* cited by examiner

BONE SIZING GUIDE

CROSS REFERENCE TO RELATED APPLICATION

This application is a National Stage 35 U.S.C. 371 of International Patent Application PCT/GB2012/052571 filed Oct. 18, 2012, claiming priority to United Kingdom applications GB1119481.8, filed Nov. 11, 2011 (now abandoned) and GB1205411.0, filed Mar. 28, 2012 (now abandoned).

BACKGROUND OF THE INVENTION

The present invention relates generally to sizing guide for a bone, especially for a femur. In particular, the present invention relates to a femoral sizing guide for determining a required size of a femoral implant and for accurately positioning a cutting block on a resected distal portion of a femur in order to locate cutting planes for preparing the end of the femur to receive the femoral implant. The femoral sizing guide incorporates a rotation mechanism to allow rotational movement between two components. The present invention controls the effect of the rotation mechanism upon the determination of required femoral implant size. The present invention also relates to methods of using the femoral sizing guide.

During the lifetime of a patient, it may be necessary to perform a joint replacement procedure on the patient as a result of, for example, disease or trauma. The joint replacement procedure, or joint arthroplasty, may involve the use of a prosthetic implant which is coupled to one of the patient's bones.

During performance of a joint replacement procedure, it is generally important to provide the orthopaedic surgeon with a certain degree of flexibility in the selection of the correct size of prosthetic implant. In particular, the anatomy of the bone to which the implant is to be coupled may vary somewhat from patient to patient. In order to implant a prosthetic joint, it is commonly necessary to prepare the bone to receive the prosthesis. For a prosthetic knee joint, both the distal femur and the proximal tibia may need to be accurately resected to shape the ends of the bones to receive the implants. For preparing the distal femur as a first preparatory step, a transverse surface is formed at the distal end of the femur by performing a first resection. This resection may be located using separate instruments, not described in detail here.

Femoral knee implants are typically provided in a range of standard sizes. Once selected, the femoral implant must be located and oriented to provide appropriate rotational alignment. Correct selection of the size of implant and correct positioning of the femoral implant relative to the natural bone is essential to ensure natural movement of the assembled joint. In particular, the implant must be positioned to provide an appropriate gap between the femur and the tibia when the knee is in extension and in flexion, and to ensure that the surrounding tissues are correctly balanced. It is known to set the rotation of the femoral implant relative to Whiteside's line, which extends from the intercondylar notch to the patella groove. Alternatively, the rotation of the femoral implant may be set relative to the transepicondylar axis, which connects the high points of the epicondyles. Further anatomical reference marks may also be used.

It is known to use a femoral sizing guide mounted on a resected distal femoral surface to measure the size of the distal femur in order to determine the appropriate size of femoral implant. The size of a femoral implant is determined by the anterior-posterior size of the implant measured parallel to an anterior-posterior implant axis. The anterior-posterior implant axis extends perpendicularly from a plane which is normal to a distal resected surface of the femur (when the implant is in its final implanted position) and in contact with the posterior condyles of the femoral implant. The anterior-posterior size of a femoral implant is the distance from this posterior condyle plane to the anterior tip of the implant. For an implant intended to be implanted without any rotation relative to the natural position of the condyles, the anterior posterior size of the femur is measured parallel to an anterior-posterior femoral axis. The anterior-posterior femoral axis extends perpendicularly from a plane which is normal to the distal resected femoral surface and in contact with the natural posterior condyles of the femur. The distal resected femoral surface is usually perpendicular to the anatomical longitudinal axis of the femur. The anterior-posterior size of the femur is the distance from the posterior condyle plane to a planned implanted position of the anterior tip of the implant. The measurement position on the anterior surface of the femur representing the planned implanted position of the anterior tip of the implant varies according to the size of the selected femoral implant. Measurement of the anterior-posterior size of a natural femur will be described below for certain known femoral sizing guides and in greater detail below in connection with embodiments of the present invention.

It is also known to use a femoral sizing guide to specify the required locations of guiding apertures into the femur to secure an appropriate cutting block to the femur for preparing the femur to receive the implant. A surgical instrument set for performing a knee replacement procedure including a femoral sizing guide is marketed by DePuy Orthopaedics, Inc. under the trade mark Sigma High Performance Instruments (Sigma HP Instruments). The Sigma HP instrument set allows surgeons to perform total knee arthroplasty procedures under most surgical approaches.

The Sigma HP femoral sizing guide is used to determine the correct size for the femoral implant and to position guide pins to support a cutting block on the distal end of the femur. A body portion of the femoral sizing guide is seated upon the resected femoral surface. Posterior feet extend from the body underneath the posterior condyles. The femoral sizing guide is correctly located when the posterior condylar surfaces rest upon the feet with Whiteside's line extending generally centrally through the sizing guide. When the feet are correctly located the body can be secured to the bone with pins which extend into the bone through fixed position pin holes. A stylus is coupled to the body such that it can be raised and lowered and locked in position. The stylus tip extends over the anterior cortex of the distal femur. The stylus can also rotate about an axis extending generally parallel to the resected surface and can slide through the coupling to the body along the anterior cortex generally parallel to the longitudinal axis of the femur. The tip of the stylus is positioned upon the anterior cortex of the femur at the intended exit point of the anterior cut for the femoral implant (which corresponds to the implanted position of the anterior tip of the corresponding implant). The height of the stylus tip above the condylar feet corresponds to the anterior-posterior distance and can be read off a scale upon the body. The measured anterior-posterior distance indicates the size of the required implant.

A scale on the stylus indicates the size of implant. The chosen size of the femoral implant determines the size of cutting block to be coupled to the distal transverse surface of the femur. The stylus position sliding through the sizing guide and the height of the stylus above the feet are set to the same value on the respective scales (corresponding to the size of the femoral implant). When the tip of the stylus just contacts the anterior cortex as the stylus sweeps across the anterior cortex, the anterior part of the corresponding size of femoral implant will terminate at the anterior surface of the bone without leaving a notch or an overhang.

There are two alternative surgical approaches for positioning a femoral implant using the Sigma HP instrument set. These are termed "posterior up" and "anterior down". Posterior up is based upon accurately positioning the cutting block relative to the posterior side of the distal femur (specifically, the posterior condylar surfaces as referenced by the feet of the sizing guide). Anterior down is based upon accurately positioning the cutting guide relative to the anterior side of the distal femur (specifically, the tip of the stylus). For the existing Sigma HP femoral sizing guide, the positioning of guide pins to support the cutting block (for making the anterior, posterior and chamfer cuts) is determined by coupling separate guide blocks to the femoral sizing guide.

The guide blocks and the position at which they couple to the rest of the sizing guide vary according to whether the chosen approach is posterior up or anterior down. Furthermore, the posterior up and anterior down blocks are available in four versions each which relate to different degrees of external rotation of the femoral implant relative to Whiteside's line or the transepicondylar axis (0°, 3°, 5° and 7° of external rotation viewed from the perspective of the surgeon observing the distal end of the femur). For an anterior down approach the guide blocks couple to the sizing guide close to the stylus and comprise wings which extend downwards over the transverse distal surface of the femur and include drill guides for positioning guide pins to support the selected cutting block. The guide blocks further comprises a blade which indicates alignment with Whiteside's line. For a posterior up approach the guide blocks couple to the sizing guide close to the pins securing the body to the bone, above the feet. The posterior up guide blocks comprise wings which extend over the transverse distal surface of the femur and include drill guides. The guide blocks further comprise a reference surface which indicates alignment with the transepicondylar axis.

Once the cutting block pins have been positioned, the femoral sizing guide including the guide block can be removed and the appropriate cutting block (according to the selected size of femoral implant) can be positioned over the guide pins to perform the anterior, posterior and chamfer cuts.

U.S. Pat. No. 6,458,135 (assigned to Howmedica Osteonics Corp.) discloses a femoral sizing guide for determining the required size of femoral implant and for determining the required location of alignment holes for securing a cutting block to the distal end of a femur. The femoral sizing guide comprises a sizing block connected to a foot component for selective pivotal movement about a pivot axis extending axially along the femur. The foot component comprises a pair of feet positioned against the posterior condylar surfaces. The centre of rotation is between the feet. A detent mechanism restricts rotational movement to predetermined angular positions. A locking mechanism is released and the device is manually turned and locked in the required position. The sizing block is positioned upon a resected transverse distal surface of the femur. Rotation of the sizing block relative to the foot component (and hence rotation of the position of the alignment holes to be drilled through the sizing block) allows the rotational position of the femoral implant about the femur to be varied. The size of femoral implant required can be determined either using guide structures upon the sizing block or via a stylus coupled to the sizing block.

For the Howmedica device, the position of the alignment holes is directly referenced to the posterior condylar surfaces through the selection of appropriate drill guide bushings to couple to the sizing block which correspond to the selected size of femoral prosthesis. For the Howmedica instrument set a single cutting block is used for performing an initial anterior cut, and the position of the anterior cut varies as each drill guide bushing adjusts the position of the alignment holes relative to the foot component. Further adjustment of the position of the anterior cut is provided through a sliding coupling between the sizing block and the foot component. The Howmedica femoral sizing block therefore only allows a surgeon to follow a posterior up surgical approach.

U.S. Pat. No. 7,488,324 (assigned to Biomet Manufacturing Corporation) discloses a modular femoral sizing guide which facilitates the selection and orientation of a femoral implant. A base portion is coupled to a resected transverse distal surface of the femur. An extension portion has a pair of feet to be positioned under the posterior condylar surfaces. The extension portion is rotatably coupled to the base portion. The centre of rotation is between the feet. A superstructure portion has a pair of drill guides to prepare alignment holes extending axially into the femur to couple a cutting block to the distal femur. The superstructure further comprises a stylus to determine the required size of the femoral implant.

To position the alignment holes, the Biomet femoral sizing guide comprises a first actuator to rotate the extension portion relative to the base portion (thereby rotating the drill guides about the femoral axis). The sizing guide further comprises a second actuator to adjust the height of the superstructure relative to the base portion (thereby raising or lowering the drill guides relative to the feet).

For the Biomet device, the position of the alignment holes is referenced to the stylus tip by control of the second actuator to lower the stylus and hence the drill guides until the tip of the stylus contacts the anterior cortex. Consequently, the Biomet femoral sizing block therefore only allows a surgeon to follow an anterior down surgical approach.

It is an aim of embodiments of the present invention to obviate or mitigate one or more of the problems associated with the prior art, whether identified herein or elsewhere. In particular it is an aim of embodiment of the present invention to provide a femoral sizing guide in which a rotation mechanism allows portion of the sizing guide to rotate relative to one another while controlling the effect of that rotation upon measurement of the anterior-posterior distance of the femur.

BRIEF SUMMARY OF THE INVENTION

According to a first aspect of the present invention there is provided a bone sizing guide for assessing the size of an end of a bone, the bone sizing guide comprising: a body comprising a foot component having a first surface to rest against an end surface of the bone and a foot extending transverse to the first surface to contact a side surface of the bone, a superstructure coupled to the body so that the superstructure can slide relative to the body towards and away from the body, at least one of the superstructure and the body being adjustable so that the rotational direction in which the superstructure extends relative to the foot component about a first axis extending transverse to the first surface is adjustable, a stylus extending from the superstructure transverse to the first surface of the body, the stylus having a tip to contact a surface of the bone, a scale coupled to or formed on a first one of the superstructure and the body, and an indicator coupled to or formed on a second one of the superstructure and the body to identify a position on the scale, in which the identified position on the scale shifts as the superstructure slides towards or away from the body, and the identified position shifts as the superstructure rotates relative to the body without sliding motion between the superstructure and the body, such that the identified position on the scale is indicative of the distance between the stylus and the foot.

An advantage of the first aspect of the present invention is that the effect of rotation of the femoral sizing guide when selecting the appropriate size of femoral implant is controlled, which facilitates the correct selection of a required size of femoral implant. The identified position on the scale changes both as the superstructure slides relative to the body and as the rotational direction of the superstructure relative to the foot component is adjusted. In order to ensure that the identified position on the scale remains the same at each rotational position when assessing the size of a femur it is necessary to also slide the superstructure relative to the body to counteract the shift in the identified position due to the rotation. The present invention allows the selection of the required rotation and the selection of the appropriate size of the femoral implant to be performed independently of one another.

The rotational direction in which the superstructure extends relative to the foot component may be selectable from a group of predetermined rotational positions. The position of the indicator mark on the second one of the superstructure and the body can be selected according to the rotational position of the superstructure relative to the foot component which is selected by the surgeon. For example, the indicator may comprise a group of indicator marks identifying different positions on the scale, each indicator mark corresponding to a respective rotational position of the superstructure relative to the foot component. The rotational positions can be predetermined positions. Alternatively, the indicator may be coupled to the second one of the superstructure and the body so that the indicator can slide relative to the second one of the superstructure and the body, the sliding position of the indicator corresponding to a rotational position of the superstructure relative to the foot component. The sliding position of the indicator can be selected from one of a group of predetermined sliding positions which correspond to a group of predetermined rotational positions of the superstructure relative to the foot component.

The body may further comprise an extension component coupled between the foot component and the superstructure such that the extension component extends from the foot component in an adjustable rotational direction about the first axis and the superstructure can slide relative to the extension component, in which the scale is coupled to or formed on the superstructure or the extension component and the indicator is coupled to or formed on the superstructure, the extension component or the foot component.

The superstructure or the body may further comprise at least one guide hole defining an alignment axis extending transverse to the first surface. The at least one alignment axis may be at a predetermined distance from the stylus or the first axis in the plane of the first surface. The superstructure may further comprise a first guide hole defining a first alignment axis at a predetermined distance from the level of the stylus tip in the plane of the first surface, and in which the body may define a second guide hole defining a second alignment axis extending into the resected femoral surface at a predetermined distance from the first axis, the distance between the first and second guide holes varying as the superstructure slides relative to the body.

The foot component may comprise first and second feet to contact side surfaces of a bone, the first and second feet defining a foot plane which extends transverse to the first surface.

The foot component may further comprise at least one fixing hole arranged to receive a fixation pin to secure the body to an end surface of a bone.

The superstructure may comprise a head part and first and second arms extending from the head part towards the body such that they are in sliding contact with the body. The bone sizing guide may further comprise a support rod extending from the body and received in a bore in the head part of the superstructure such that as the superstructure slides relative to the body the support rod passes through the bore. The stylus may comprise an elongate slot arranged to couple to the head part of the superstructure such that the stylus extends from the superstructure transverse to the support rod, the stylus slot being arranged to allow the stylus to slide relative to the support rod and to rotate about the support rod.

According to a second aspect of the present invention there is provided a method of assessing the size of an end of a bone, the method comprising: coupling a body of a bone sizing guide to the bone, the body comprising a foot component and a foot extending transverse to the first surface, so that the first surface rests against an end surface of the bone and the foot contacts a side surface of the bone, adjusting the rotational position of a superstructure coupled to the body relative to the foot component about a first axis extending transverse to the first surface until the superstructure extends from the foot component in a predetermined rotational direction, sliding the superstructure relative to the body towards or away from the body until a tip of a stylus extending from the superstructure transverse to the first surface of the body contacts a surface of the bone, and recording a position on a scale coupled to or formed on a first one of the superstructure and the body identified by an indicator coupled to or formed on a second one of the superstructure and the body, in which the identified position on the scale shifts as the superstructure slides towards or away from the body, and the identified position shifts as the superstructure rotates relative to the body without sliding motion between the superstructure and the body, such that the identified position on the scale is indicative of the distance between the stylus and the foot.

The superstructure may be coupled to the body so that the rotational position of the superstructure relative to the foot component can be set to a selected rotational position and the indicator may comprise a group of indicator marks identifying different positions on the scale, each indicator mark corresponding to a rotational position of the superstructure relative to the foot component. The method may further comprise: setting the superstructure relative to the body to a rotational position, selecting an indicator mark corresponding to the selected rotational position, and recording the position on the scale identified by the selected indicator mark. The rotational positions can be predetermined rotational positions.

BRIEF DESCRIPTION OF THE DRAWINGS

Embodiments of the present invention will now be described, by way of example only, with reference to the accompany drawings, in which.

DETAILED DESCRIPTION OF THE INVENTION

Figure 1:
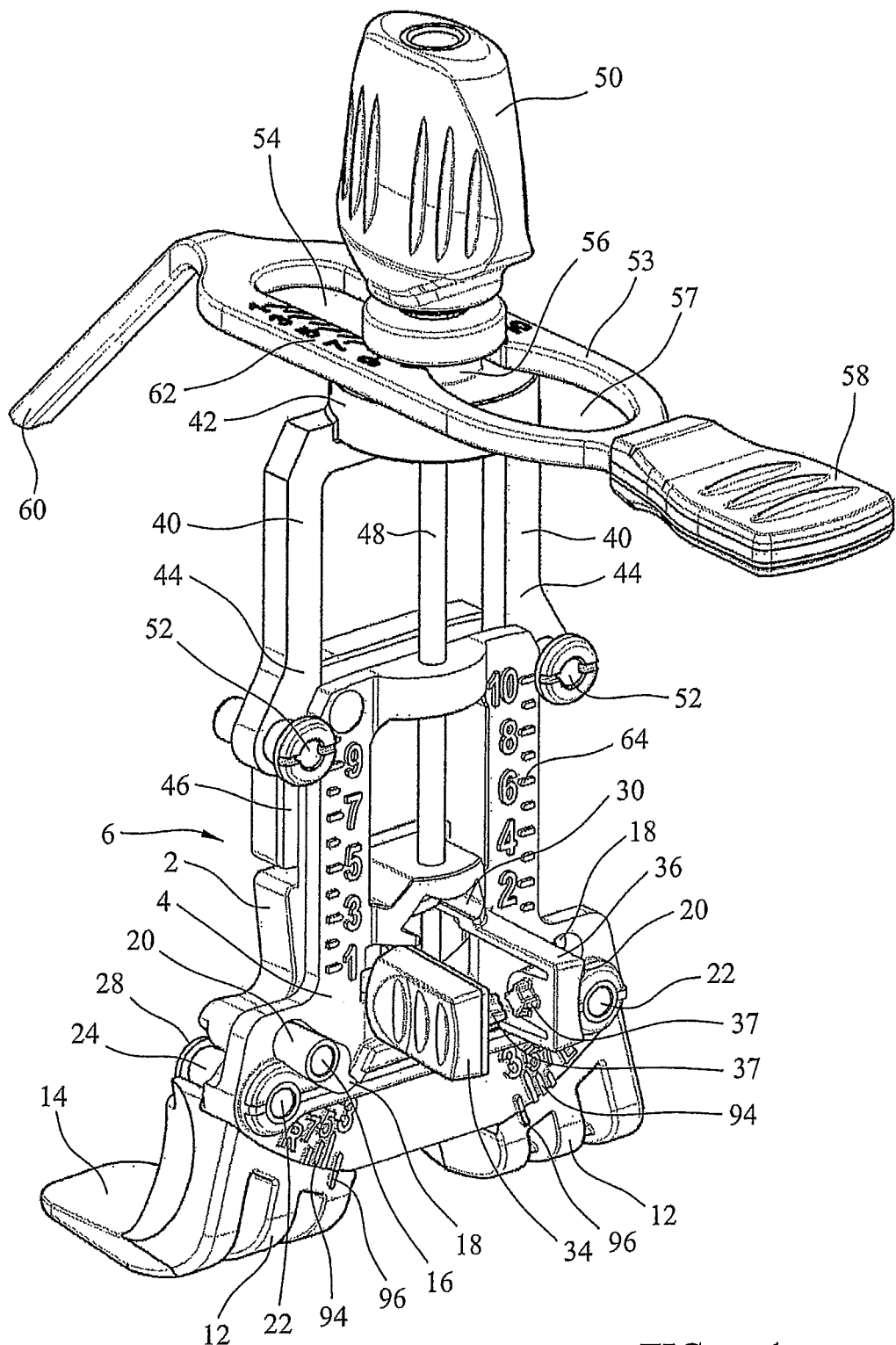
FIGS. 1 and 2 illustrate first and second views of a femoral sizing guide from different perspectives.

Before a femoral sizing guide in accordance with an embodiment of the present invention can be used, the distal end of the femur must undergo initial resection to remove a distal portion of the femur to establish a surface which is transverse to the longitudinal axis of the femur. The femoral sizing guide is arranged to either allow alignment holes to be drilled into the resected surface or to place guide pins extending from the resected surface. Specifically, femoral sizing guides in accordance with embodiments of the present invention include drill guide holes which allow either holes to be drilled into the resected surface of the bone or guide pins to be directly inserted into the bone passing through the drill guides. The femoral sizing guide fixes the position of the alignment holes/guide pins at a predetermined distance relative the posterior condyles or the anterior cortex and at a rotational position about the axis of the femur. The alignment holes or guide pins are used to position a cutting block upon the surface of the bone to perform the shaping resections of the end of the femur. Consequently, the position of the alignment holes or guide pins determines the final implanted position of the femoral implant.

As noted above in connection with the known Sigma HP femoral sizing guide, there are two principal options for positioning a cutting block to prepare a distal end of a femur to receive a femoral implant: anterior down and posterior up. The choice is dependent partially upon surgeon preference. An anterior down approach prevents notching of the anterior cortex of the distal femur, or the femoral implant overhanging the anterior cortex, at the expense of less control over the position of the prosthetic posterior condyles. A posterior up approach allows accurate control of the position of the posterior condyles and therefore better control of the joint tension when the knee is in flexion. The femoral implants may be provided in a range of sizes with regular size increments. For instance, the femoral implants may be provided in increments of 3 mm, though it will be appreciated that other increments are possible. Femoral sizing guides in accordance with embodiments of the present invention are required to locate guide holes or pins extending into the resected surface at a predetermined distance from either the anterior cortex or the posterior condyles irrespective of the selected size of the femoral implant. The stylus provides a guide to the appropriate size implant and therefore cutting block. As the position of the guide pins is selected using the femoral sizing guide, the cutting blocks can be designed to have a fixed distance between the pin holes and the position of the bone cuts, rather than requiring that the cutting blocks allow the position of the bone cut to be adjusted relative to the pin positions. The cutting block may provide a further adjustment mechanism allowing the surgeon to control the position of the cutting block relative to the anterior cortex or posterior condyles. For an exemplary range of femoral implants having 3 mm size increments, the cutting blocks may be arranged to allow the position of each cutting block relative to the guide pin or guide holes (and therefore relative to the anterior cortex or posterior condyles) to vary within ±1.5 mm. This allows for flexibility to accommodate femurs which fall between standard sizes of the femoral implant. The cutting block adjustment mechanism may comprise a series of three holes to receive each guide pin. A first hole is at the normal position and the other holes are 1.5 mm above and below the first hole.

Figure 2:
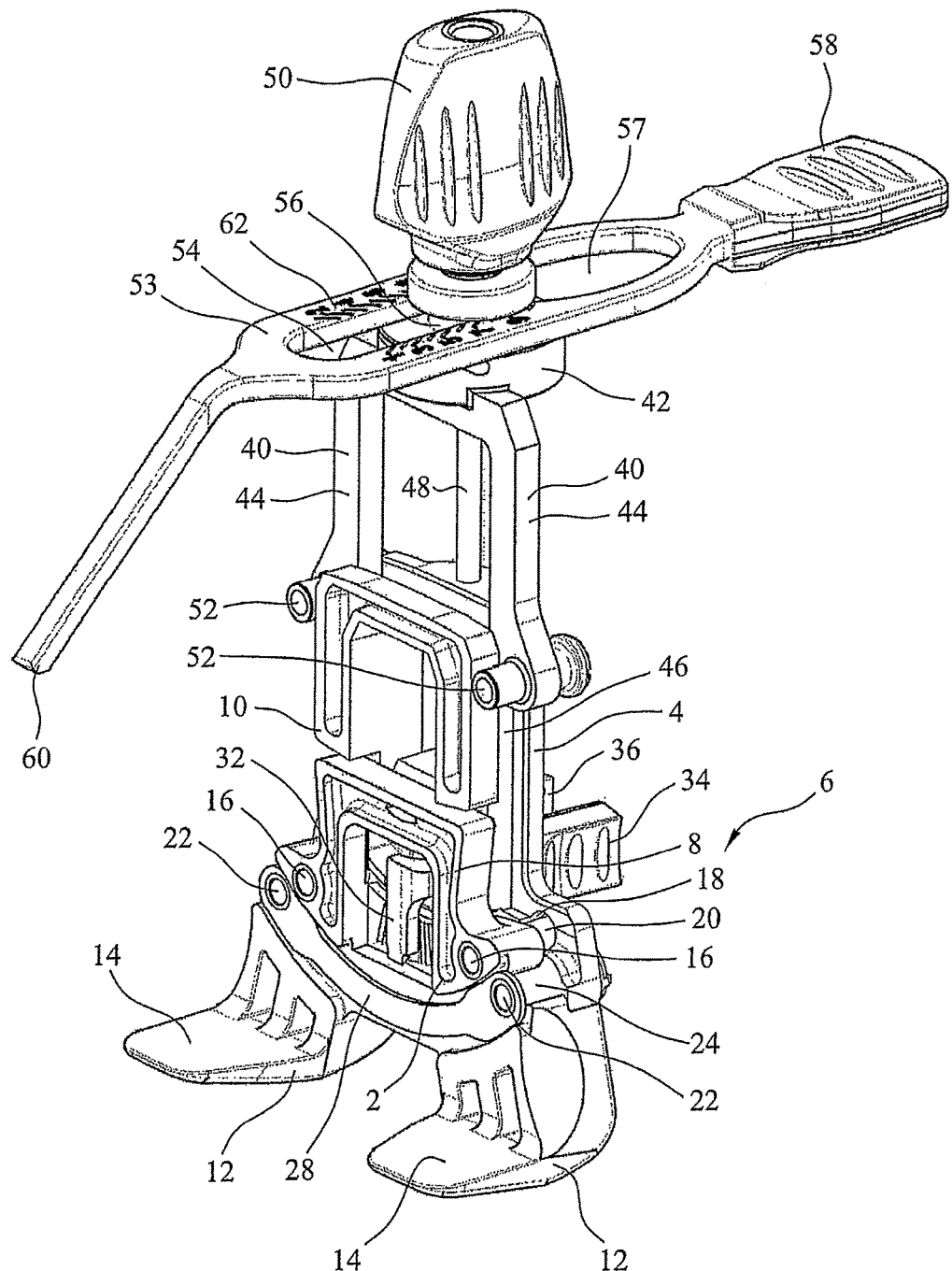
Figure 3:
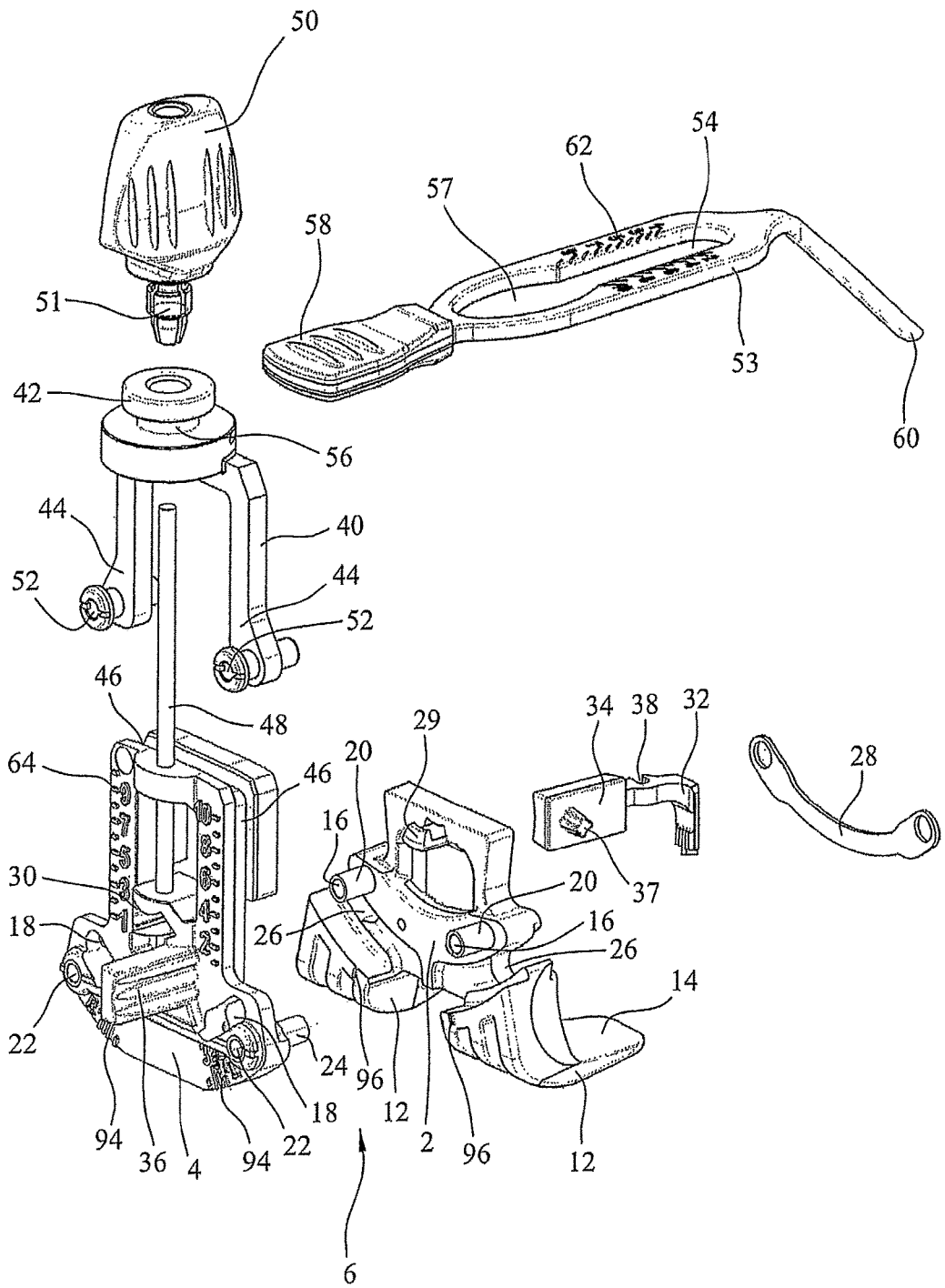
FIGS. 3 and 4 illustrate exploded views of the femoral sizing guide of FIGS. 1 and 2 from different perspectives.
Figure 4:
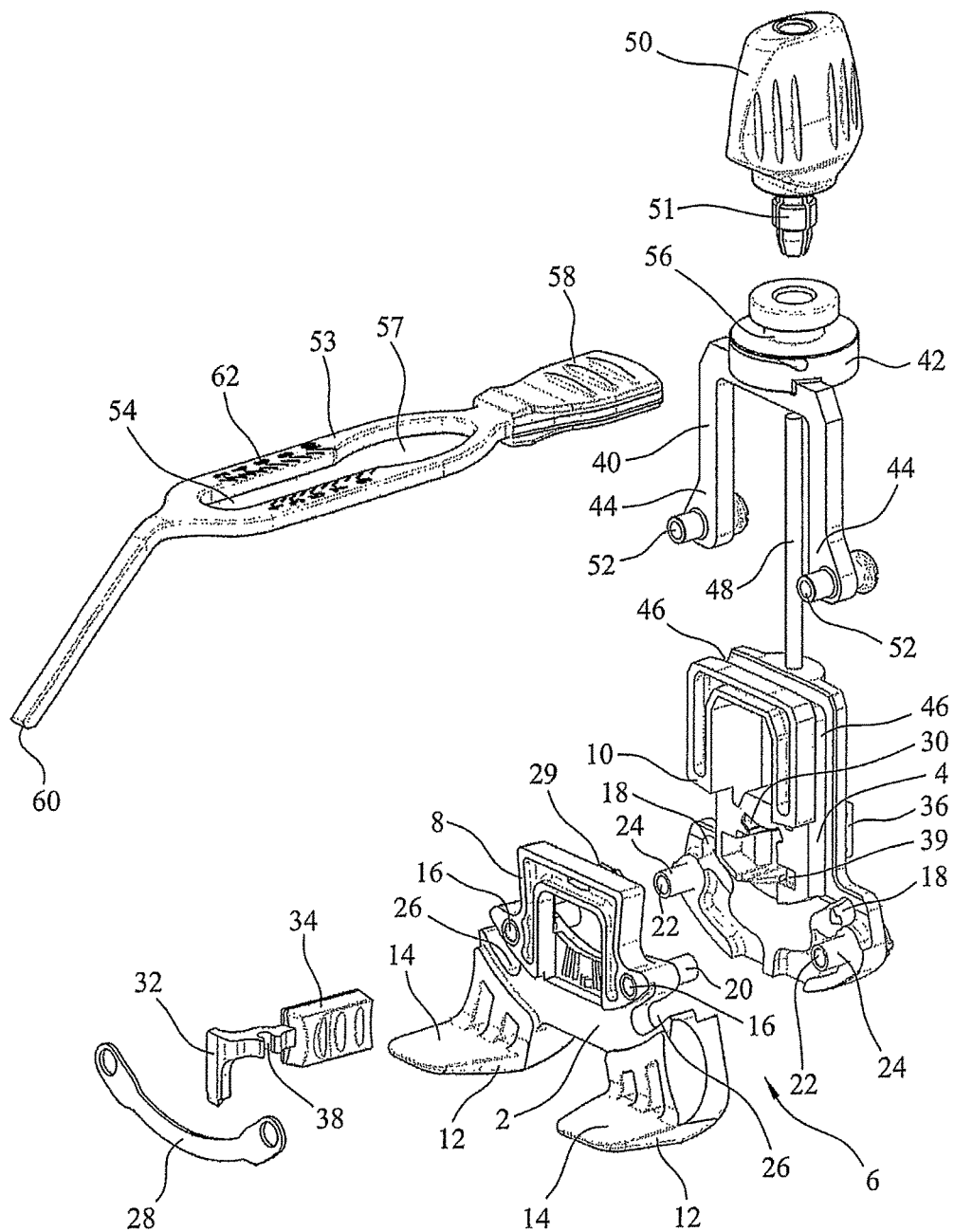

FIGS. 1 and 2 illustrate perspective views of a femoral sizing guide. FIGS. 3 and 4 illustrate exploded views of the femoral sizing guide. The femoral sizing guide comprises a foot component 2 and an extension piece 4, collectively forming a body 6. The foot component 2 and the extension piece 4 are rotatably coupled together as will be described in greater detail below. The foot component 2 comprises a first side 8 (visible in FIGS. 2 and 4) which in use is placed against the resected distal surface of the femur. Similarly the extension piece 4 also has a first surface 10 (visible in FIGS. 2 and 4) to bear against the femur. The foot component 2 comprises first and second feet 12 which in use extend underneath the posterior condyles. In particular, foot locator surfaces 14 are arranged to bear against respective posterior condylar surfaces to locate the femoral sizing guide on the resected femoral surface relative to the position of the posterior condyles. The foot component 2 further comprises first and second pin holes 16. When the femoral sizing guide is correctly positioned on the resected femoral surface such that the foot locator surfaces bear against respective posterior condylar surfaces fixing pins are driven into the resected bone surface through pin holes 16 to secure the femoral sizing guide in place preventing further movement of the foot component 2 relative to the femur.

The extension piece 4 is rotatably coupled to the foot component 2 such that when the foot component 2 is pinned to the femur the extension piece can rotate by sliding over the bone surface as it rotates. The centre of rotation is generally positioned between the feet 12 such that when the femoral sizing guide is pinned to the bone the centre of rotation is generally aligned with Whiteside's line. However, for the femoral sizing guide shown in FIGS. 1 to 6 there is no pivotal connection at the centre of rotation. This allows the surgeon a clear view of Whiteside's line, which assists with determining the required rotational alignment of the femoral implant. For the femoral sizing guide in accordance with an embodiment of the invention shown in FIGS. 10A and 10B there is a pivotal connection at the centre of rotation. The extension piece 4 comprises first and second arcuate grooves 18 which are defined by a curve radiating from the centre of rotation of the foot component 2 and the extension piece 4. Each groove 18 is arranged to receive an extended sleeve portion 20 of a foot component pin hole 16 such that as the extension piece 4 rotates relative to the foot component 2 its movement is constrained by the pin holes sleeves 20 sliding through grooves 18. The range of rotational movement of the extension piece 4 relative to the foot component 2 is limited by the pin hole sleeves 20 bearing against closed outer ends of the arcuate grooves 18.

The extension piece 4 further comprises a first pair of guide holes 22 for determining the axes of alignment holes or guide pins extending into the resected femur for a posterior up approach, as will be described in greater detail below. The guide holes 22 comprise sleeve portions 24 which extend through arcuate grooves 26 formed in the foot component 2. The foot component slots 26 are open ended as they extend to the edge of the foot component 2 and are defined by a curve having the same origin but a larger radius of curvature than the radius of curvature for the extension piece slots 18. As the extension piece 4 rotates relative to the foot component 2 the guide hole sleeves 24 slide along foot component grooves 26. The range of rotational movement of the extension piece 4 relative to the foot component 2 is further limited by the guide hole sleeves 24 bearing against the closed ends of foot component grooves 26.

To secure the extension piece 4 to the foot component 2 a retaining bar 28 extends between the guide hole sleeves 24 such that the foot component 2 is sandwiched between the extension piece 4 and the retaining bar 28. To provide further stability to the assembled femoral sizing guide, a spigot 29 (not visible in FIGS. 1 and 2) extends from the foot component 2 into an arcuate slot 30 formed in the extension piece 4 such that the spigot 29 slides within slot 30 as the extension piece rotates relative to the foot component 2. The arcuate slot 30 is defined by a curve having its origin at the centre of rotation between the foot component 2 and the extension piece 4.

A locking mechanism is provided to lock the extension piece 4 to the foot component 2 at predetermined rotational positions. The locking mechanism comprises a lever 32 which is pivotally coupled to the extension piece 4. The lever 32 is operated by trigger 34, specifically by squeezing trigger 34 against bar 36 which extends outwardly from the extension piece 4. The lever 32 is biased towards the foot component 2 by a spring (not illustrated) which extends between lugs 37 formed on the trigger 34 and the bar 36 such that when the trigger 34 is released the lever bears against the foot component 2 to prevent further rotation of the extension piece. The lever 32 comprises a groove 38 which couples to a bar 39 formed within the extension piece 4 to allow the lever to rotate relative to the extension piece 4. It will be appreciated that alternative mechanisms for coupling the lever 32 to the extension piece 4 are possible, the only requirement being that relative movement between the lever 32 and the foot component 2 is provided to allowing locking and unlocking. For instance, a pin may be provided press fitted into a hole formed in lever 32 generally at the position of groove 38. The pin may be received and rotate within a hole in extension piece 4. The locking mechanism is described in greater detail below.

The femoral sizing guide further comprises a superstructure 40 which is coupled to the extension piece 4 and arranged to slide relative to the extension piece 4 generally towards and away from the feet 12. The superstructure 40 comprises a head part 42 and arms 44 which extend downwardly and are arranged to slide within channels 46 formed in the sides of the extension piece 4. A support rod 48 extends upwards from the central part of the extension piece 4 and passes through the superstructure head 42. The support rod 48, together with arms 44 sliding in channels 46 serve to control sliding movement of the superstructure 40 and to prevent twisting of the superstructure 40 relative to the extension piece 4 as it slides. The superstructure 40 can be locked in position relative to the extension piece 4 by tightening locking knob 50, which compresses a collet 51 (visible in FIGS. 3 and 4) over the support rod 48.

The superstructure 40 further comprises a second pair of guide holes 52 positioned towards the free ends of the arms 44. The second pair of guide holes 52 is used as an alternative to the extension piece guide holes 22 for determining the axes of alignment holes extending into the resected femur for an anterior down approach, as will be described in greater detail below. The superstructure guide holes 52 comprise sleeves such that in use the tips of the sleeves are contact with the resected bone surface.

The femoral sizing guide further comprises a stylus 53 coupled to the head part 42 of the superstructure 40. The stylus 53 is arranged to extend over the distal end of the femur when the femoral sizing guide is coupled to the resected distal surface of the femur. The stylus 53 is coupled to the superstructure 40 such that it extends from head part 42 substantially at 90° to the axis of support rod 48. The stylus 53 comprises an elongate slot 54 arranged to engage a neck 56 of the head part 42 so that the stylus can slide relative to the head part 42 and can rotate about the body part 42. The stylus slot 54 further comprises an enlarged portion 57 arranged to pass over the upper side of head part 42 and the locking knob 50 to detach the stylus 53 from the femoral sizing guide. The stylus 53 further comprises a handle 58 at a first end to rotate the stylus 53 relative to the superstructure 40 and to slide the slot 54 over the neck 56 of the superstructure 40.

At the second end, the stylus 53 is bent downwards towards a stylus tip 60. The stylus tip 60 is arranged to contact the anterior cortex of the femur by sliding and rotating the stylus 53 relative to the superstructure 40 and by sliding the superstructure 40 relative to the extension piece 4. The stylus 53 has a scale 62 marked along both sides of slot 54. Each mark on the scale 62 corresponds to a selected size of femoral implant. The position of the stylus is indicated by the mark on the stylus scale 62 adjacent to head part 42 on the stylus handle side of the body part 42. Similarly, the extension piece 4 further comprises a scale 64 marked along both sides of the extension piece 4. Each mark on the extension piece scale 64 corresponds to a selected size of femoral implant. The position of the superstructure 40 relative to the extension piece 4 is indicated by the mark on the superstructure scale 64 adjacent to the centre of the superstructure guide holes 52. Stylus scale 62 and superstructure scale 64 both indicate the same range of sizes of femoral implant. When the superstructure 40 and the stylus 53 are both positioned at corresponding locations on scales 64, 62 then the stylus tip 60 indicates the exit point on the anterior cortex for the selected size of femoral implant. Both the superstructure 40 and the stylus 53 are adjusted in unison according to their respective scales until the stylus tip 60 is just in contact with the anterior cortex of the bone as the stylus tip 60 is swept across the anterior cortex. The scales 62, 64 then indicate the required size of femoral implant, as will be described in greater detail below in connection with the remainder of the surgical technique for using the femoral sizing guide.

Figure 5A:
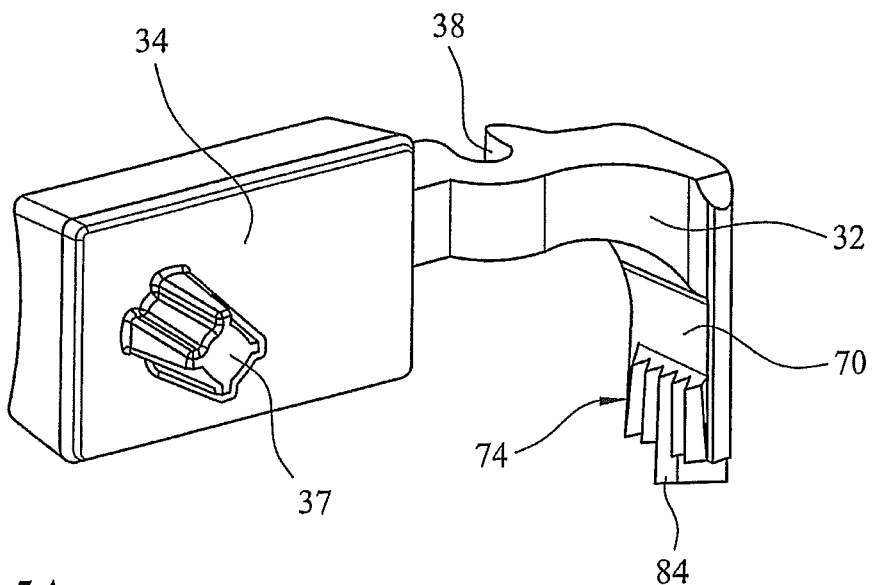
FIGS. 5A and 5B illustrate enlarged views of parts of the locking mechanism of the femoral sizing guide of FIGS. 1 and 2.
Figure 5B:
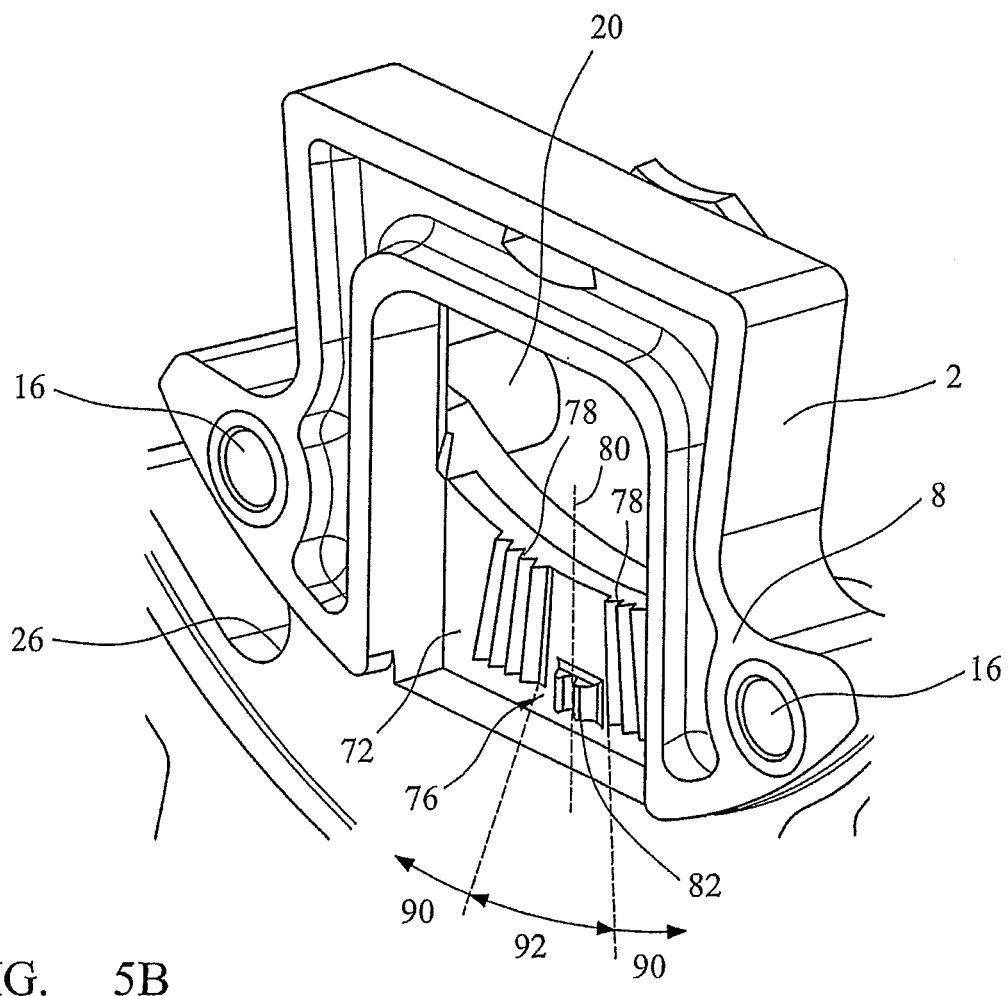

Referring now to FIGS. 5A and 5B these illustrate enlarged portions of the femoral sizing guide locking mechanism in order that the operation of the locking mechanism may be more clearly understood. FIG. 5A illustrates lever 32 separated from the extension piece 4. Lever 32 is illustrated from the same perspective as the exploded view of FIG. 3. FIG. 5B illustrates part of the foot component 2 separated from the extension piece 4. The foot component 2 is illustrated from the same perspective as the exploded view of FIG. 4. The lever 32 of FIG. 5A and the foot component of FIG. 5B are viewed from different perspectives so as to allow the portions of each component that face one another to be viewed.

As noted above, the lever 32 is coupled to the extension piece 4 such that it can rotate into and out of contact with the foot component 2 to lock the rotational position of the extension piece 4 relative to the foot component 2. The lever 32 is biased towards the foot component 2, but the bias can be overcome by the surgeon squeezing trigger 34 towards bar 36. The lever 32 has a lever face 70 which bears against a ratchet plate 72 on the foot component 2. The lever face 70 has an array of teeth 74 which bear against a curved ratchet 76 on the ratchet face 72. When the trigger 34 is squeezed against bar 36 teeth 74 are disengaged from the curved ratchet 76. The extension piece 4 can be freely rotated relative to the foot component 2 within a predetermined rotational range limited by movement of sleeves 20 and 24 within respective slots 18 and 26.

When the trigger 34 is released, the teeth 74 engage the curved ratchet 76 causing the orientation of the extension piece 4 relative to the foot component 2 to be limited to a series of predetermined rotational positions. For instance, the locking mechanism may be arranged to allow the extension piece 4 to be locked relative to the foot component 2 at 0° (which corresponds to a symmetrically upright position). As the extension piece 4 rotates relative to the foot component 2 the vertical rod 48 also rotates. Rod 48 serves as a visual reference to the correct rotational position of the extension piece. The correct rotational position of the extension piece 4 relative to the foot component 2 is indicated when rod 48 is aligned with Whiteside's line, which generally corresponds to an anterior to posterior axis for the distal femur. Additionally, horizontal lines formed in the visible end of guide sleeves 52 serve as a visual reference for aligning the rotation of the extension piece relative to the transepicondylar axis. Rotation of the extension piece 4 relative to the foot component 2 may be locked at ±3°, 5° and 7° relative to the 0° position. While the locking mechanism is released the extension piece 4 may be freely rotated until the rod 48 is brought into alignment with Whiteside's line. The locking mechanism may then be engaged. The interaction of the teeth 74 with the curved ratchet 76 serves to cause the position of the extension piece 4 relative to the foot component 2 to settle at the closest position. Advantageously, although the locking mechanism is small, it still allows accurate selection of 0° and ±3°, 5° or 7° of offsets. This selection is achieved by having two sets of grooves within the curved ratchet 76. An upper ratchet 78 has a 2° pitch and is provided in two separate portions with a space in between. Each portion of the upper ratchet 78 is aligned with ±3°, 5° or 7° grooves relative to a centerline 80. The grooves in the upper ratchet 78 are arranged to engage corresponding teeth 74 on the lever face 70. Consequently, the upper ratchet 76 allows the orientation of the extension piece 4 relative to the foot component 2 to be fixed at predetermined positions (±3°, 5° or 7°) within first portions of the predetermined rotational range indicated by arrows 90.

The curved ratchet 76 further comprises a second, lower ratchet 82 which comprises a single groove aligned with the 0° position. It will be appreciated that the second ratchet 82 may overlap with the first ratchet 78, as illustrated in FIG. 5B so long as there is a sufficient difference in alignment to allow the first ratchet to be engaged without interference from the second ratchet, and vice versa, as will now be described. The lever teeth 74 have an elongated central tooth 84 which is arranged to engage lower ratchet groove 82 when the lever is centrally positioned across curved ratchet 76. There is only a single groove 84 within a second, central portion of the predetermined rotational range of the extension piece 4 relative to the foot component 2 indicated by arrow 92. Consequently, the extension piece 4 can only be locked relative to the foot component at a single position within the second portion 92 of the predetermined rotational range. It will be appreciated that in alternative femoral sizing guides there may be more than two separate portions of the predetermined rotational range, each supporting ratchets which are arranged to be separately engaged by the lever 32 to allow the extension piece to be locked relative to the foot component. Furthermore, within each portion of the rotational range the corresponding ratchet may be arranged to allow the orientation of the extension piece relative to the foot component to be locked at one or more predetermined orientations, according to the number of grooves. Groove 82 has broad shoulders preventing the central lever tooth 84 from settling at other positions within the second portion 92 of the rotational range. The upper ratchet 78 has a gap in the second portion 92 of the rotational range. This prevents the remainder of the lever teeth from clashing with the upper ratchet. As the central lever tooth 84 comprises an extension of a tooth at the same pitch as the remainder of the lever teeth 74 when the lever engages the upper ratchet in the first portions of the rotational range the central tooth 84 meshes with the upper ratchet 76.

Figure 6:
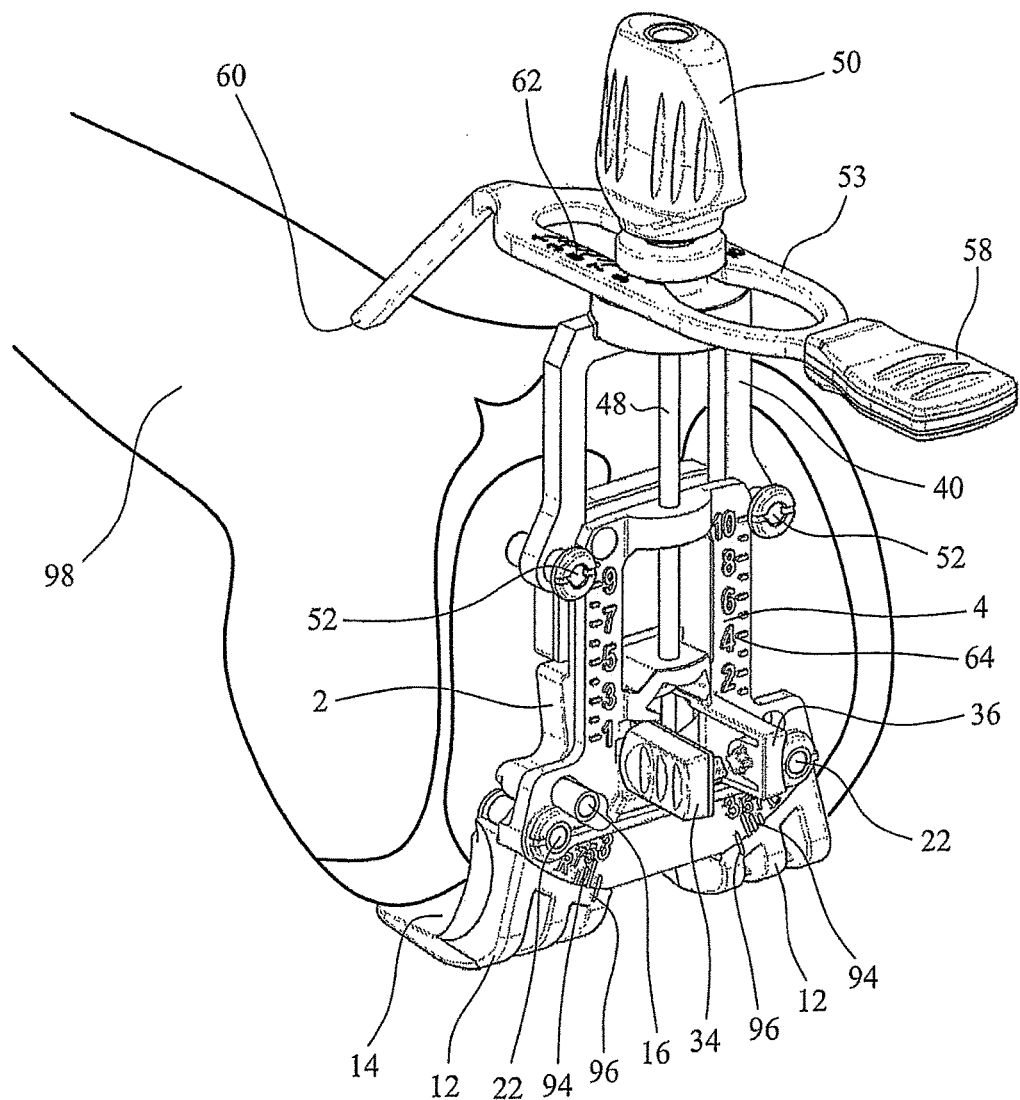
FIG. 6 illustrates the femoral sizing guide of FIG. 1 coupled to a resected surface at the end of a femur, FIGS. 7 and 8 schematically illustrate front and side views respectively of a femoral sizing guide superimposed over the corresponding implanted position of a selected femoral implant, FIGS. 9A to 9D schematically illustrate the problem of a femoral sizing guide inaccurately measuring the anterior-posterior size of a femur when the femoral sizing guide is rotated.

A method of using the femoral sizing guide described above will now be described in connection with FIG. 6 which illustrates the femoral sizing guide coupled to a resected distal portion of a femur 98. The foot component 2 is positioned against the end of the bone such that surface 8 is in contact with the bone and feet 12 extend underneath and contact the posterior condyles. The foot component is then moved across the resected surface until the foot locator surfaces 14 bear against the posterior condylar surfaces (that is, the femoral sizing guide is centrally located on the end of the bone. The femoral sizing guide can then be secured to the bone by passing fixing pins through holes 16 in the foot component into the bone.

The rotational alignment of the extension piece (and hence the rotational alignment of the guide pins for securing the cutting block and the resulting femoral implant) can then be set. The required rotational alignment may be determined during pre-operative planning or intra-operatively using anatomical landmarks, for instance by rotating the extension piece 4 relative to the foot component 2 until the rod 48 is aligned with Whiteside's Line. The rotation is set by squeezing the trigger 34 and bar 36 together to release the locking mechanism and then manually rotating the extension piece 4 and superstructure 40. When the required rotation is set and checked on scale 94 on the extension piece relative to a mark 96 on the foot component, the locking mechanism is engaged by releasing trigger 34.

As discussed above, the sizing guide can be set to varying sizes of femoral implant by adjusting the height of the superstructure 40 relative to scale 64 on the extension piece 4. The superstructure 40 is raised and lowered by releasing and tightening locking knob 50 to cause collet 51 to grip or release the rod 48. Additionally, the position of the stylus 53 is set by sliding stylus slot 54 over extension piece neck 56 and reading the stylus position on scale 62. For each femoral implant selected for the stylus on scale 62, the superstructure should be set to the same size on scale 64. The tip 60 of the stylus is positioned on the anterior cortex of the femur at the position the surgeon has chosen for the anterior cut to exit the bone. Ideally for the chosen implant size the stylus tip should just touch the anterior cortex as the stylus tip 60 is swept across the anterior cortex. However, in practice the stylus tip may touch the anterior cortex at a position where the indication of implant size by the position of the superstructure 40 relative to the extension piece 4 is between two standard sizes of implant. Whether the next largest or next smallest implant is chosen is at the choice of the surgeon.

Guide pins to support the cutting block can then be inserted through either the lower alignment holes 22 (for a posterior up approach) or the upper alignment holes 52 (for an anterior down approach). The choice between anterior down and posterior up approaches is the same as for the Sigma HP instrument set described above. Either guide pins are inserted into the bone through the alignment holes or alignment holes may be drilled into the bone. The sizing guide is then removed and the guide pins or holes used to mount a cutting guide to perform the shaping resections for the selected size of femoral implant.

Figure 7:
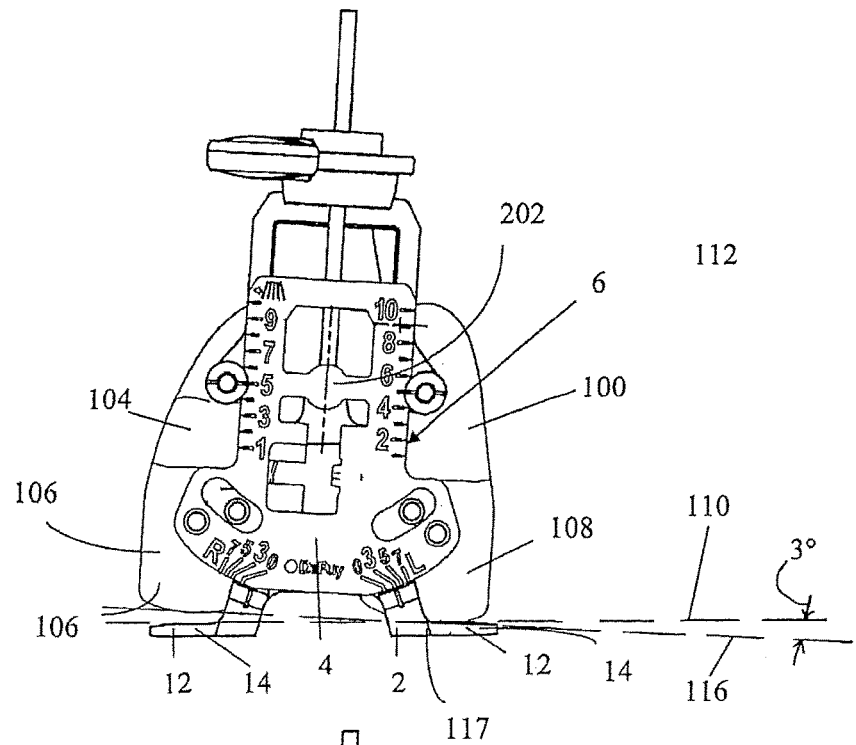
Figure 8:
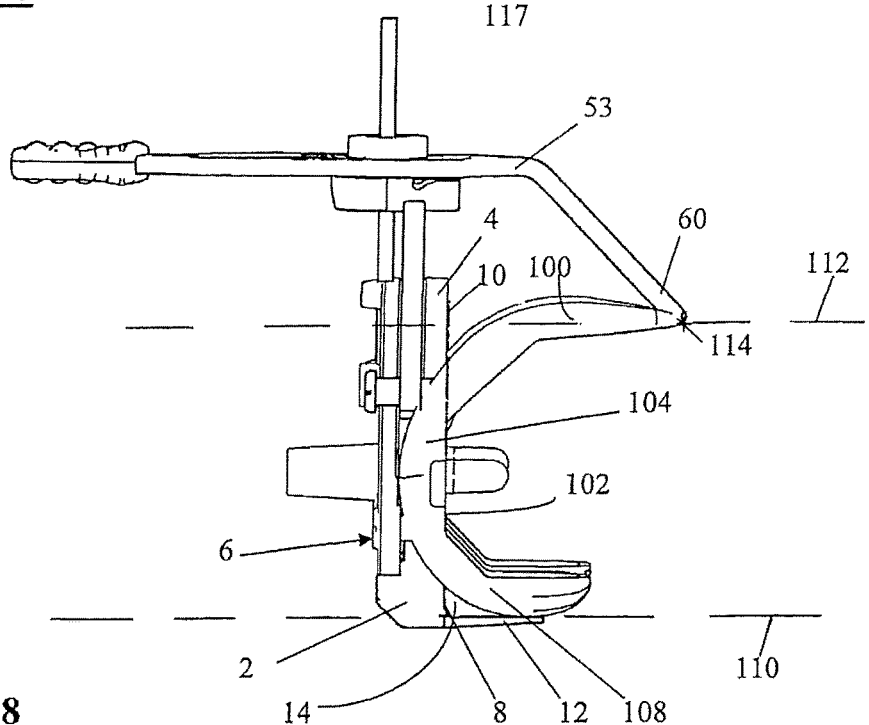

Referring now to FIGS. 7 and 8 these illustrate front and side views respectively of a femoral sizing guide in place at the distal end of a femur (the femur is not illustrated) superimposed over an image of the corresponding implanted position of a selected femoral implant 100. The femoral sizing guide shown in FIGS. 7 and 8 is generally the same as the femoral sizing guide shown in FIGS. 1 to 6 except that the pivotal connection between foot component 2 and extension component 4 has changed. Specifically, in place of the spigot 29 and slot 30 arrangement spaced apart from the centre of rotation shown in FIGS. 1 to 6, FIG. 7 shows the femoral sizing guide having a fixed pivot 202. That is, pivot 202 couples the foot component 2 and the extension 4 together so that the two parts rotate relative to one another about a pivot axis extending through the pivot into the femur. This arrangement may be more rigid than for the femoral sizing guide of FIGS. 1 to 6. Rotational movement between the two parts continues to also be controlled by the pin guide and slot arrangement described above. The femoral implant 100 is generally C shape when viewed from the side as shown in FIG. 8 and is arranged to cup the resected distal, anterior and posterior surfaces of the femur. The femoral implant 100 includes a first internal surface 102 which when implanted is seated upon the resected distal end of the femur. As discussed above, the foot part 2 and the extension part 4 of the femoral sizing guide (collectively body part 6) comprises reverse surfaces 8 and 10 respectively which in use rest upon the resected distal end of the femur. For illustrative purposes the femoral sizing guide and the femoral implant 100 are shown superimposed in FIG. 8 so that surfaces 8, 10 and 102 coincide and the distal portion 104 of the femoral implant 100 overlaps with the femoral sizing guide body part 6. Clearly the femoral implant 100 and the femoral sizing guide could not be brought together in this way as the distal portion 104 of the implant 100 and the body part 6 of the femoral sizing guide would clash.

The size of rotation of a femoral implant is dependent upon clinical indications. However, the direction of rotation is always external to the patient: clockwise for a left leg and anticlockwise for a right leg as viewed facing the distal end of the femur. FIG. 7 illustrates the femoral sizing guide from the view point of a surgeon operating a femoral sizing guide when it is in placed on the distal end of a left femur. FIG. 7 shows the femoral sizing guide set to 3° of external rotation for a left femur: the extension part 4 has been rotated 3° clockwise relative to the foot part 2. The sizing guide feet 12 are in contact with the posterior condyles of the natural femur (not illustrated). Rotation of the extension part 4 causes pin holes 22, 52 to rotate. Consequently the cutting block, the resection planes and ultimately the femoral implant are also rotated. The result is that as illustrated in FIG. 7 the medial and lateral condyles 106, 108 of the implant 100 are rotated at 3° relative to the natural condyles (the position of which is indicated by the sizing guide feet 12). The implanted position of the implant lateral condyle 108 is substantially the same as the position of the natural lateral condyle, shown in FIG. 7 by the implant lateral condyle 108 touching the lateral foot 12. The implant medial condyle 106 is raised up above the medial foot by a distance which varies with the amount of rotation.

FIGS. 7 and 8 illustrate the relationship between the measured anterior-posterior size of the femur and the size of a selected implant 100. The anterior-posterior size of implant 100 is measured between plane 116 (which extends perpendicularly to implant surface 102 and therefore to the resected distal femoral surface and is in contact with condyles 106, 108) and the anterior tip 114 of the implant 100 parallel to the anterior-posterior axis of the implant. The anterior-posterior axis of the implant is normal to plane 116.

The natural femur anterior-posterior size is measured relative to a plane 110 which extends perpendicular to the distal resected surface of the femur and contacts the natural posterior condyles. It can be seen in FIG. 7 that plane 110 intersects plane 116 along a line indicated at point 117. When the sizing guide is set to 0° of rotation the planes 110 and 116 are coincident. When the sizing guide is positioned on the femur, plane 110 includes the feet contact surfaces 14. The set anterior-posterior distance of the sizing guide can be varied by adjusting the guide as described above to increase or decrease the distance between plane 110 and the tip 60 of stylus 53. As discussed above the position of the stylus 53 is adjusted so that the tip 60 just contacts the anterior surface of the femur as the stylus is swept across the femur. As the stylus 53 is swept over the femur by rotating the stylus 53 about rod 48 the tip 60 describes a curved line in a plane 112. The position where the stylus tip 60 contacts the anterior femur surface corresponds to the exit point of the anterior resection and also the implanted position of the anterior tip 114 of the implant 100 when the sizing guide is correctly adjusted and the selected size of implant 100 exactly matches the natural femur.

As can be seen in FIG. 7, plane 116 is rotated relative to plane 110 by the same amount as the extension part 4 is rotated relative to the foot part 2. It will be appreciated that the plane 112 is parallel to the plane 116. The anterior-posterior size for the natural femur between the plane 112 of the stylus tip 60 and the plane 110 of the guide feet 12 is equal to the anterior-posterior size of the implant at the point 117 where plane 110 intersects 116. However this does not correspond directly to the anterior-posterior size indicated on scale 64. When the sizing guide is set to 0° of rotation then the anterior-posterior distance between the stylus tip plane 112 and the guide feet plane 110 is exactly equal to the anterior-posterior size of an implant corresponding to the size indicated on scales 62 and 64 on the sizing guide. For a sizing guide set with some degree of rotation, the anterior-posterior distance between the stylus tip 60 plane 112 and the foot plane 110 is not fixed as these planes are inclined to one another by the set amount of rotation. As the rotation of the sizing guide is increased the distance along a line extending normally from the plane 112 of the stylus tip 60 to the intersection 117 of planes 110 and 116 will decrease even if the superstructure 40 remains fixed relative to the body part 6 so that scale 64 records the same anterior-posterior distance. However, for a given femur the appropriate size of femoral implant does not change according to the required implanted position of the implant. When the femoral sizing guide is rotated without sliding the superstructure relative to the extension part, the corresponding size of the femoral implant 100 (the anterior-posterior size of the implant measured between planes 112 and 116) does not vary as plane 116 rotates with the sizing guide. The result of this interdependence between rotation of the sizing guide and the measured size of the femur is that as the rotation of the sizing guide increases the measured anterior-posterior size of the natural femur increases whereas the required implant size stays the same. Alternatively, it can be considered that for a femur assessed as requiring a particular size of implant at 0° of rotation, rotating the sizing guide artificially increases the assessed size of implant. This variation of the measured size of the femur with the selected amount of rotation is a source of error as will now be described in greater detail in connection with FIGS. 9A to 9D.

Figure 9A:
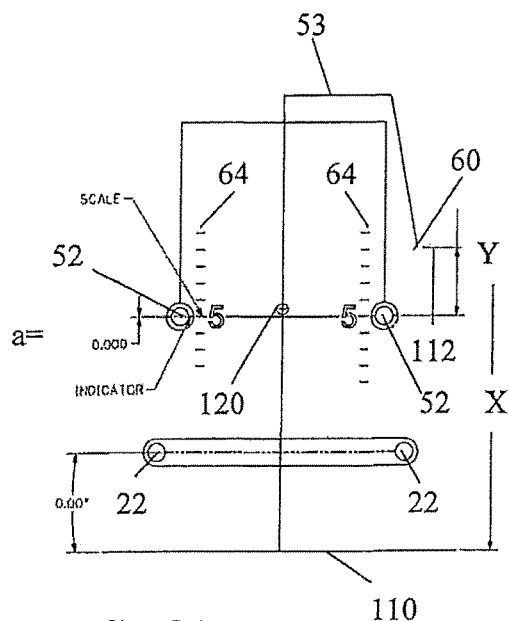

FIG. 9A schematically illustrate a femoral sizing guide adjusted to indicate implant size "5" at differing degrees of rotation within the sizing guide: 0°, 3°, 5° and 7° respectively. For a size 5 femoral implant the anterior-posterior size of the implant measured as described above is identified may be approximately 50 mm. From here onwards the anterior-posterior measurement of a size 5 femoral implant is referred to as X mm. Clearly this is fixed regardless of the implant rotation. Each of FIGS. 9A to 9D schematically show the plane 110 of the sizing guide feet, the pin guides 22 for positioning a cutting block in a posterior up surgical approach, the pin guides 52 for positioning a cutting block in an anterior down surgical approach and the stylus 53. The pin guides 22 are formed in the extension part 4 and the pin guides 52 are formed in the superstructure 40. The stylus 53 is coupled to the superstructure 40 so that the plane 112 within which stylus tip 60 moves is always at a fixed distance relative to the line joining pin guides 52 which is referred to from here onwards as Y mm. The centre of rotation between the foot part 2 and the extension part 4 (and therefore also the superstructure 40) is marked at 120. The line joining pin guides 52 is parallel to the line joining pin guides 22 and both are rotated by: 0°, 3°, 5° or 7° for each of FIG. 9A-9D respectively.

Figure 9B:
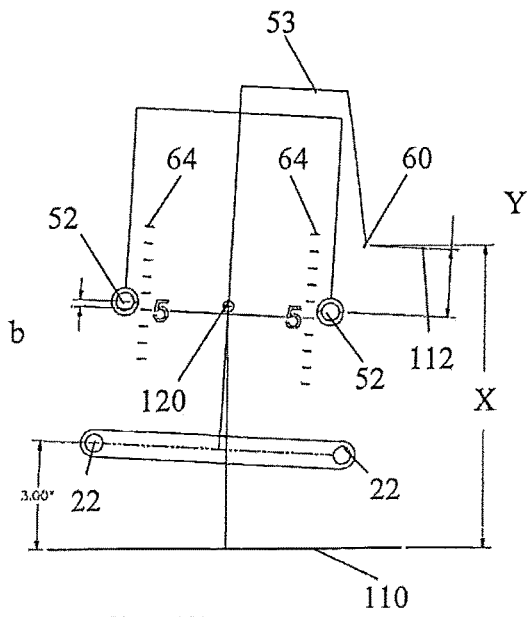
Figure 9C:
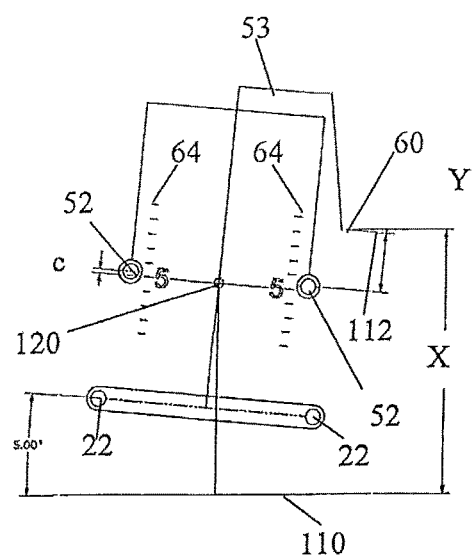
Figure 9D:
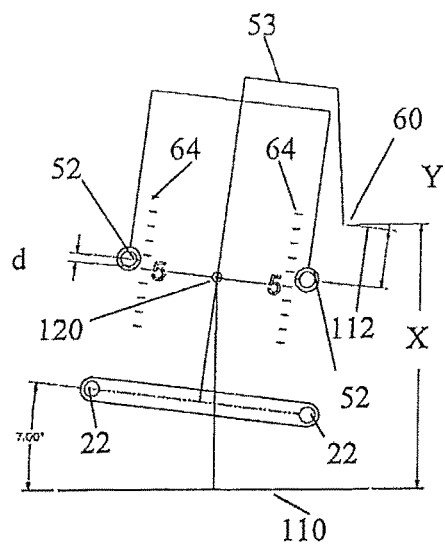

For FIG. 9A, the distance between the stylus tip 60 and the plane 110 joining the sizing guide feet is X mm. In each of FIG. 9A to 9D it is assumed that the stylus extends normally to the rest of the sizing guide, generally in line with the femoral axis. Alternatively, in place of the distance between the stylus tip 60 and the plane 110 being measured, the size of the natural femur may be considered to be measured between plane 112 and point 117 where planes 110 and 116 intersect (in which case, the rotational position of the stylus 53 about rod 48 is immaterial). The measurement position on scale 64 is indicated by the centre of pin guides 52 as shown. FIG. 9A shows the pin guides 52 being aligned with scale mark "5" on scale 64. In FIG. 9B the sizing guide is rotated by 3°. To ensure that the distance between stylus tip 60 and plane 110 continues to be X mm (that is, the distance between the stylus tip and the instrument feet corresponds to a size 5 implant) it is necessary to raise pin guides 52 upwards by distance a mm, which in one particular embodiment of the femoral sizing guide may be approximately 1.3 mm. Although only mark "5" is shown on scale 64, with reference to FIG. 1 for instance it can be seen that pin guide 52 in FIG. 9B points to a position between marks "5" and "6". Similarly, as the rotation increases in FIGS. 9C and 9D it can be seen that the position of the pin guides must be shifted by b mm and c mm respectively, which may be approximately 2.2 mm and 3.2 mm. The misalignment is approximately linear for each additional degree of rotation in the region of interest (0° to 7°). That is, for the same size femur the sizing guide significantly over-reads as the rotation of the sizing guide increases. In one particular embodiment of a femoral implant the anterior-posterior size increment between adjacent sizes of femoral implant may be 3 mm. For a rotation of 7° this over-read greater than a whole size of femoral implant.

Figure 10A:
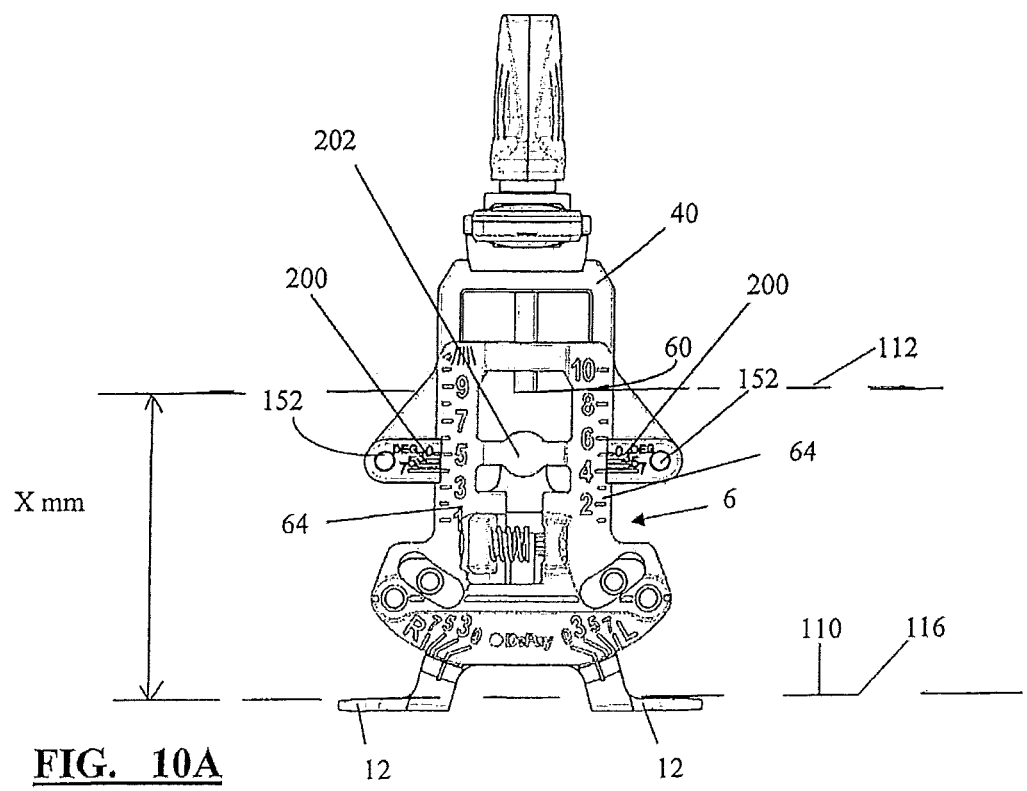
FIGS. 10A and 10B illustrate a femoral sizing guide in accordance with an embodiment of the present invention in first and second positions which addresses the problem illustrated in FIGS. 9A to 9D, and FIGS. 11A to 11D schematically illustrate an alternative partial solution to the problem illustrated in FIGS. 9A to 9D.
Figure 10B:
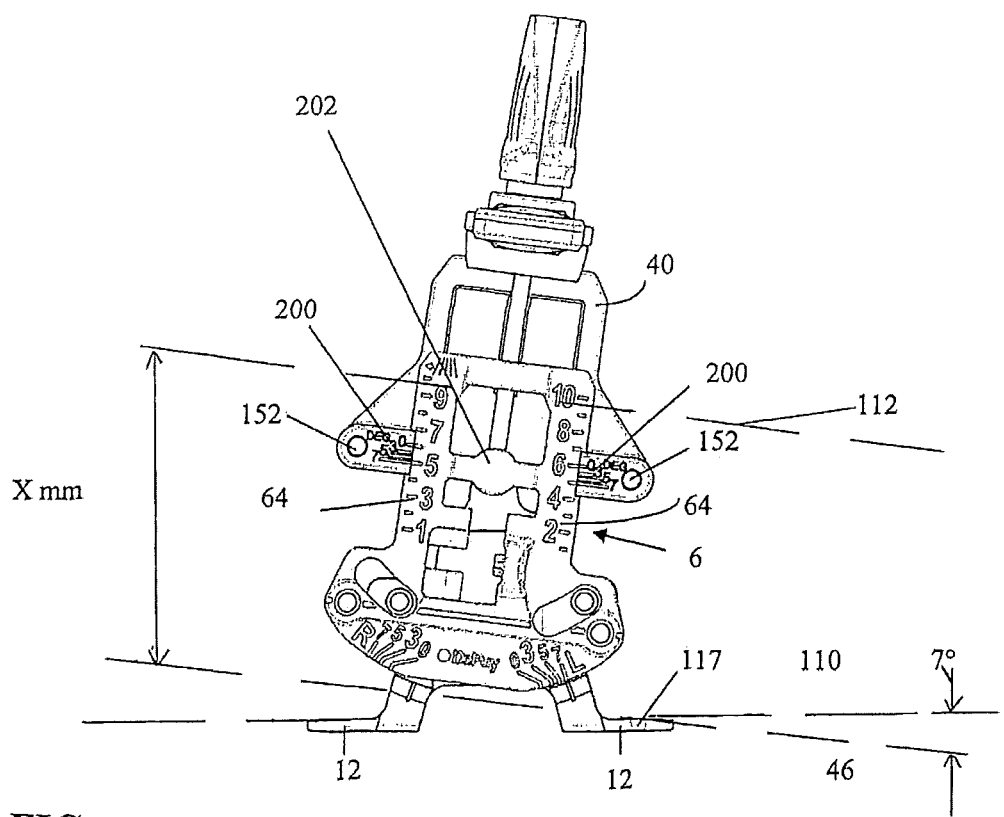
Figures 11A, 11B:
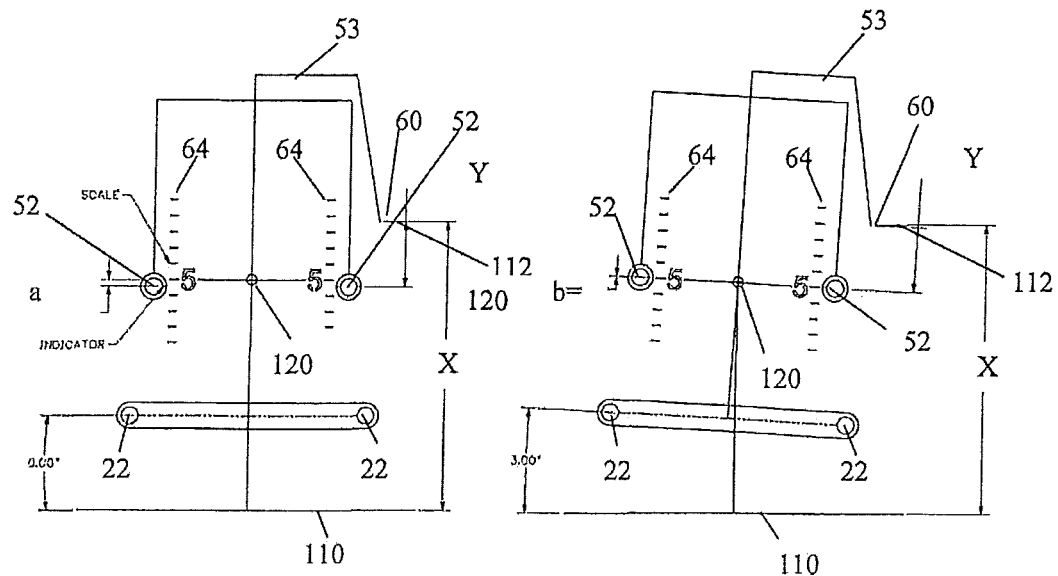
Figures 11C, 11D:
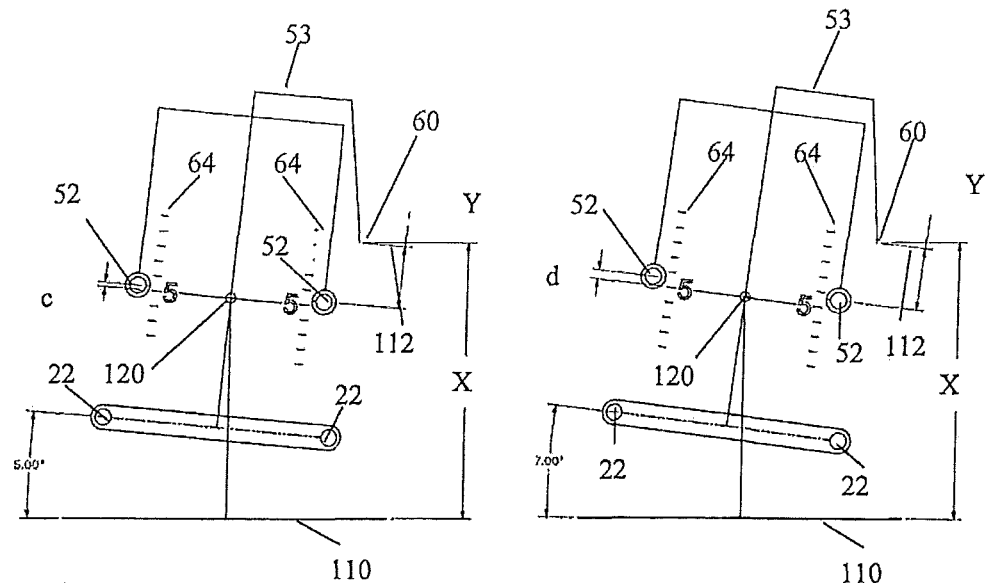

FIGS. 9A to 9D show a femoral sizing guide having a scale 64 set up to give the correct measurement of anterior-posterior size of the femur when the guide is set to 0° of rotation. As the sizing guide is rotated there is a significant offset between the scale 64 and the indicator 52. Referring now to FIGS. 10A and 10B these illustrate a femoral sizing guide in accordance with an embodiment of the invention which addresses this error. The femoral sizing guide shown in FIGS. 10A and 10B is generally the same as that described above in connection with FIGS. 1 to 6 and so the same numbering is used except where there are differences, in which case the numbering is increased by 100. The femoral sizing guide shown in FIGS. 10A and 10B includes the same modification to the pivotal connection between the foot component 2 and the extension component 4 described above in connection with FIGS. 7 and 8.

FIG. 10A shows the femoral sizing guide set to 0° of rotation and FIG. 10B shows the femoral sizing guide set to 7° of rotation (clockwise, for a left femur). The plane 112 of stylus tip 60, the plane 10 of the natural condyles and sizing guide feet 12 and the plane 116 of the femoral implant condyles are shown in FIGS. 10A and 10B. In FIG. 10A planes 110 and 116 are coincident and in FIG. 10B planes 110 and 116 intersect at point 117 along a line at 7° approximately at the location of the lateral natural and implant condyles. In both FIGS. 10A and 10B the distance between planes 112 and 116, which is the anterior-posterior size of the implant, is the same: X mm. In FIG. 10B the distance between the stylus tip plane 112 and the foot plane 110 is only equal to X mm at the intersection 117 of planes 110 and 116. It can be seen that in order to ensure that the distance between planes 112 and 116 remains constant the superstructure 40 is raised up in FIG. 10B relative to FIG. 10A away from the body part 6. However, the scale 64 is unchanged. To allow the scale 64 to be read to give a consistent measure of the anterior-posterior size of a femur as the rotation is increased, instead of a single scale indicator at the position of pin holes 152 the sizing guide of FIGS. 10A and 10B includes an indicator comprising four indicator marks 200. Each indicator mark 200 is labelled with a corresponding rotation reference (0°, 3°, 5°, 7°).) In order to read scale 64 correctly it is necessarily only that the rotation of the sizing guide is set and then the corresponding indicator 200 is used. The position of indicators 200 can be readily adjusted in different embodiments to accommodate differences in the variation of anterior-posterior size with rotation and for sizing guides which allow the rotation to be set to different amounts.

In accordance with alternative embodiments of the present invention the scale 64 and scale indicators 200 of FIGS. 10A and 10B may vary. For instance the scale may be provided on the arms 44 of the superstructure and the indicators on the extension part 4 of the guide. Alternatively, the indicator may comprise a separate component coupled to either the superstructure or the extension part so that it can slide. The sliding position of the indicator component may be set according to the selected rotation. As a further alternative there may be an array of different scales with a different scale for each possible rotation, each scale having a single fixed indicator.

As a further alternative there may be a single scale positioned on the superstructure arranged to slide relative to the extension part as the superstructure (and the stylus) is raised up and down. However, in place of an indicator mounted on the extension part, the indicator is coupled directly to the foot component so that as the sizing guide is rotated the superstructure (and hence the scale) rotates relative to the indicator. It will be appreciated that in such an embodiment the position of the scale relative to the centre of rotation of the guide will control the amount by which the indicator moves relative to the scale as the guide is rotated. The indicator may comprise a bar extending from the foot component so that the bar overlaps the scale such that the position on the scale is identified by the edge of the bar (or the bar could be transparent to allow the scale to be read against a indicator line on the bar). The scale may be repositioned on the other side of the pivot axis compared with the illustrated embodiment of FIGS. 10A and 10B.

In a further embodiment of the invention the indication of the rotation of the sizing guide and the sliding position of the superstructure may be combined. The pivot point 202 shown in FIGS. 7, 10A and 10B may be utilised to indicate both the rotation and the implant size. The pivot point 202 is adapted so that it comprises a front piece which is rigidly fixed to the foot component such that it does not move relative to the feet when the extension part rotates but does move relative to the adjacent portions of the extension component. This front piece is provided with an indicator mark and the extension piece surrounding the front part of the pivot is provided with a rotary scale. As the sizing guide is rotated the front piece indicator mark points to a position on the rotary scale. The identified position on the rotary scale is indicative of the size of rotation between the extension component and the foot component. However, each mark on the rotary scale serves a dual purpose in that each mark is extended to reach the linear scale 64 on the superstructure. In order to read the linear scale 64 to determine the required size of femoral implant the appropriate mark on the rotary scale is identified using the indicator on the front part of the pivot point, that mark forming an indicator for the linear scale 64.

As an alternative to providing a scale and indicator which can adjust according to the selected degree of rotation, in a further embodiment illustrated in FIGS. 11A to 11D the position of the scale on the extension part (or alternatively the superstructure) is adjusted so that is accurate at 3° of rotation (FIG. 9B) and is misaligned at alternative amounts of rotation. FIGS. 11A to 11D are generally the same as FIGS. 9A to 9D and show the sizing guide set to 0°, 3°, 5° and 7° of rotation respectively. Ensuring that the scale is accurate at 3° of rotation is advantageous for two reasons. Firstly, 3° of rotation is the most commonly selected rotation and so the sizing guide will be accurate for the majority of patients. Secondly, the maximum misalignment remains at 7°, but the size of the misalignment is significantly less than the maximum misalignment when the scale is set to be accurate at 0° as shown in FIGS. 9A to 9D. Clearly the sizing guide of FIGS. 11A to 11D is a compromise relative to that of FIGS. 10A and 10B. However, with the adjusted scale of FIGS. 11A to 11D there is a reduced risk of the scale being misread compared with the multiple scale indicators solution of FIGS. 10A and 10B.

In accordance with an alternative embodiment of the present invention in place of the rotation mechanism between the foot component and the extension component described above there may be provided a set of foot components each arranged to couple to a single extension component at a different rotational position. In such an embodiment the complexity of the sizing guide is reduced at the expense of increasing the number of separate components. Such a sizing guide may in particular be a single use instrument intended to be discarded after use, and so reducing the complexity (and therefore cost) of the instrument is desirable. In such an embodiment the scale and indicator mechanism may be similar or identical to that described above.

It will be readily apparent to the appropriately skilled person that further modifications may be made to the present invention and further applications may be found for the present invention from the teaching herein, without departing from the scope of the appended claims.

The invention claimed is:

1. A bone sizing guide for assessing the size of an end of a bone, the bone sizing guide comprising:
a body comprising a foot component having a first surface to rest against an end surface of the bone and a foot extending transverse to the first surface to contact a side surface of the bone,
a superstructure coupled to the body so that the superstructure can slide relative to the body towards and away from the body, at least one of the superstructure and the body being adjustable so that a rotational direction in which the superstructure extends relative to the foot component about a first axis extending transverse to the first surface is adjustable,
a stylus extending from the superstructure transverse to the first surface of the body, the stylus having a tip to contact a surface of the bone,
a scale coupled to or formed on a first one of the superstructure and the body, and
an indicator coupled to or formed on a second one of the superstructure and the body to identify a position on the scale,
in which the identified position on the scale shifts as the superstructure slides towards or away from the body, and the identified position shifts as the superstructure rotates relative to the body without sliding motion between the superstructure and the body, such that the identified position on the scale is indicative of the distance between the stylus and the foot.

2. The bone sizing guide of claim 1, in which the rotational direction in which the superstructure extends relative to the foot component is selectable from a group of predetermined rotational positions.

3. The bone sizing guide of claim 1, in which the position of the indicator mark on the second one of the superstructure and the body which is used to identify the said position on the scale can be selected according to the rotational position of the superstructure relative to the foot component which is selected by the surgeon.

4. The bone sizing guide of claim 1, in which the indicator comprises a group of indicator marks identifying different positions on the scale, each indicator mark corresponding to a respective rotational position of the superstructure relative to the foot component.

5. The bone sizing guide of claim 1, in which the indicator is coupled to the second one of the superstructure and the body so that the indicator can slide relative to the second one of the superstructure and the body, the sliding position of the indicator corresponding to the rotational position of the superstructure relative to the foot component.

6. The bone sizing guide of claim 1, in which the body further comprises an extension component coupled between the foot component and the superstructure such that the extension component extends from the foot component in an adjustable rotational direction about the first axis and the superstructure can slide relative to the extension component, in which the scale is coupled to or formed on the superstructure or the extension component and the indicator is coupled to or formed on the superstructure, the extension component or the foot component.

7. The bone sizing guide of claim 1, in which the superstructure or the body further comprises at least one guide hole defining an alignment axis extending transverse to the first surface.

8. The bone sizing guide of claim 7, in which the at least one alignment axis is at a predetermined distance from the stylus or the first axis in a plane of the first surface.

9. The bone sizing guide of claim 7, in which the superstructure further comprises a first guide hole defining a first alignment axis at a predetermined distance from a level of the stylus tip in a plane of the first surface, and in which a body defines a second guide hole defining a second alignment axis extending into the resected femoral surface at a predetermined distance from the first axis, the distance between the first and second guide holes varying as the superstructure slides relative to the body.

10. The bone sizing guide of claim 1, in which the foot component comprises first and second feet to contact side surfaces of a bone, the first and second feet defining a foot plane which extends transverse to the first surface.

11. The bone sizing guide of claim 1, in which the foot component further comprises at least one fixing hole arranged to receive a fixation pin to secure the body to an end surface of a bone.

12. The bone sizing guide of claim 1, in which the superstructure comprises a head part and first and second arms extending from the head part towards the body such that they are in sliding contact with the body.

13. The bone sizing guide of claim 12, further comprising a support rod extending from the body and received in a bore in the head part of the superstructure such that as the superstructure slides relative to the body the support rod passes through the bore.

14. The bone sizing guide of claim 13, in which the stylus comprises an elongate slot arranged to couple to the head part of the superstructure such that the stylus extends from the superstructure transverse to the support rod, the stylus slot being arranged to allow the stylus to slide relative to the support rod and to rotate about the support rod.

15. A method of assessing the size of an end of a bone, the method comprising:
   coupling a body of a bone sizing guide to the bone, the body comprising a foot component and a foot extending transverse to a first surface, so that the first surface rests against an end surface of the bone and the foot contacts a side surface of the bone,
   adjusting a rotational position of a superstructure coupled to the body relative to the foot component about a first axis extending transverse to the first surface until the superstructure extends from the foot component in a predetermined rotational direction,
   sliding the superstructure relative to the body towards or away from the body until a tip of a stylus extending from the superstructure transverse to the first surface of the body contacts a surface of the bone, and
   recording a position on a scale coupled to or formed on a first one of the superstructure and the body identified by an indicator coupled to or formed on a second one of the superstructure and the body,
   in which the identified position on the scale shifts as the superstructure slides towards or away from the body, and the identified position shifts as the superstructure rotates relative to the body without sliding motion between the superstructure and the body, such that the identified position on the scale is indicative of the distance between the stylus and the foot.

16. The method of claim 15, in which the superstructure is coupled to the body so that the rotational position of the superstructure relative to the foot component is set at a selected rotational position and the indicator comprises a group of indicator marks identifying different positions on the scale, each indicator mark corresponding to a respective rotational position of the superstructure relative to the foot component, the method further comprising:
   setting the superstructure relative to the body to a selected rotational position,
   selecting an indicator mark corresponding to the selected rotational position, and
   recording the position on the scale identified by the selected indicator mark.

* * * * *